United States Patent
Nowak et al.

(10) Patent No.: US 12,178,872 B2
(45) Date of Patent: Dec. 31, 2024

(54) REGULATORY T CELL EXPRESSING A CHIMERIC ANTIGEN RECEPTOR

(71) Applicants: Miltenyi Biotec B.V. & Co. KG, Gladbach (DE); Charite-Universitätsmedizin Berlin, Berlin (DE)

(72) Inventors: Anna Nowak, Berlin (DE); Dominik Lock, Cologne (DE); Andrew Kaiser, Rösrath (DE); Alexander Scheffold, Berlin (DE)

(73) Assignees: Miltenyi Biotec B.V. & Co. KG, Bergisch Gladbach (DE); Charité—Universitätsmedizin Berlin, Berlin (DE)

( * ) Notice: Subject to any disclaimer, the term of this patent is extended or adjusted under 35 U.S.C. 154(b) by 1117 days.

(21) Appl. No.: 16/962,755

(22) PCT Filed: Jan. 17, 2019

(86) PCT No.: PCT/EP2019/051143
§ 371 (c)(1),
(2) Date: Jul. 16, 2020

(87) PCT Pub. No.: WO2019/141774
PCT Pub. Date: Jul. 25, 2019

(65) Prior Publication Data
US 2020/0353004 A1   Nov. 12, 2020

(30) Foreign Application Priority Data

Jan. 19, 2018 (EP) .................... 18152631

(51) Int. Cl.
| | |
|---|---|
| C07K 14/725 | (2006.01) |
| A61K 35/12 | (2015.01) |
| A61K 39/00 | (2006.01) |
| C07K 14/705 | (2006.01) |
| C07K 16/44 | (2006.01) |
| C12N 5/0783 | (2010.01) |

(52) U.S. Cl.
CPC ...... *A61K 39/4611* (2023.05); *A61K 39/4621* (2023.05); *A61K 39/4631* (2023.05); *A61K 39/464* (2023.05); *C07K 14/7051* (2013.01); *C07K 14/70517* (2013.01); *C07K 14/70521* (2013.01); *C07K 14/70578* (2013.01); *C07K 16/44* (2013.01); *C12N 5/0637* (2013.01); *A61K 2035/122* (2013.01); *A61K 2239/22* (2023.05); *C07K 2317/622* (2013.01); *C07K 2319/02* (2013.01); *C07K 2319/03* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 9,523,076 B2 | 12/2016 | Schonbrunn et al. | |
| 10,617,720 B2* | 4/2020 | Eckardt | A61K 39/001154 |
| 11,890,300 B2* | 2/2024 | Lock | A61K 39/464412 |
| 2005/0208079 A1 | 9/2005 | Cassone et al. | |
| 2009/0214566 A1 | 8/2009 | Cassone et al. | |
| 2011/0097313 A1 | 4/2011 | Schönbrunn et al. | |
| 2017/0274095 A1* | 9/2017 | Meyer | C07K 14/7051 |
| 2019/0388468 A1* | 12/2019 | Lock | C07K 14/705 |

FOREIGN PATENT DOCUMENTS

| | | |
|---|---|---|
| CN | 102153651 B | 11/2012 |
| CN | 106163547 | 11/2016 |
| CN | 107106670 | 8/2017 |
| CN | 107557342 A | 1/2018 |
| WO | 2306191 | 4/2011 |
| WO | WO 2017/042170 | 3/2017 |
| WO | WO 2017/075433 | 5/2017 |
| WO | WO 2017/100428 | 6/2017 |
| WO | WO 2017/143094 | 8/2017 |
| WO | WO 2017/147383 | 8/2017 |
| WO | WO 2019/141774 | 7/2019 |

OTHER PUBLICATIONS

Barrett et al., 2015, Chimeric Antigen Receptor- and TCR-Modied T Cells Enter Main Street and Wall Street, J. Immunol., 195 (3): 755-761 (Year: 2015).*

Blaeschke et al., "Defined central memory and stem memory T cell phenotype of CD4 and CD8 CAR T cells for the treatment of CD19+ acute lymphoblastic leukemia in an automated closed system," Abstract Only, Blood, Dec. 2, 2016, 128(2), 2 pages.

Blaeschke et al., "Induction of a central memory and stem cell memory phenotype in functionally active CD4+ and CD8+ CAR T cells produced in an automated good manufacturing practice system for the treatment of CD19+ acute lymphoblastic leukemia," Cancer Immunology, Immunotherapy, Jul. 1, 2018, 67(7):1053-1066.

(Continued)

*Primary Examiner* — Jessica H Roark
(74) *Attorney, Agent, or Firm* — Christian Biervert; Fish & Richardson P.C.

(57) ABSTRACT

The present invention provides a regulatory T (Treg) cell expressing an antigen chimeric receptor (CAR) comprising a) at least one antigen binding domain, b) a transmembrane domain, and c) a cytoplasmic signaling domain comprising at least one primary cytoplasmic signaling domain and at least the co-stimulatory signaling domain of CD137, wherein said antigen binding domain specifically binds an antigen that is expressed on the surface of a target cell or a tag of a tagged polypeptide that binds to an antigen expressed on the surface of a target cell or a soluble antigen. Compositions comprising said Treg cells, and methods of enrichment and analysis of activated Tregs that express said CAR are also disclosed.

2 Claims, 5 Drawing Sheets

Specification includes a Sequence Listing.

(56) References Cited

OTHER PUBLICATIONS

Boardman et al., "Expression of a chimeric antigen receptor specific for donor HLA class I enhances the potency of human regulatory T cells in preventing human skin transplant rejection," American Journal of Transplantation, Apr. 2017, 17(4):931-943.

Koristka et al., "Engrafting human regulatory T cells with a flexible modular chimeric antigen receptor technology," Journal of Autoimmunity, Jul. 1, 2018, 90:116-131.

MacDonald et al., "Alloantigen-specific regulatory T cells generated with a chimeric antigen receptor," The Journal of clinical investigation, Apr. 1, 2016, 126(4):1413-1424.

Nowak et al., "cD137+ cD154− expression as a regulatory T cell (Treg)-specific activation signature for identification and sorting of stable human Tregs from In Vitro expansion cultures," Frontiers in Immunology, Feb. 7, 2018, 9:199.

Noyan et al., "Prevention of allograft rejection by use of regulatory T cells with an MHC-specific chimeric antigen receptor," American Journal of Transplantation, Apr. 2017, 17(4):917-930.

PCT International Preliminary Report on Patentability in International Application. No. PCT/EP2019/051143, dated Jul. 21, 2020, 7 pages.

PCT International Search Report and Written Opinion in International Application. No. PCT/EP2019/051143, dated Apr. 2, 2019, 6 pages.

Skuljec et al., "Chimeric antigen receptor-redirected regulatory T cells suppress experimental allergic airway inflammation, a model of asthma," Frontiers in Immunology, Sep. 12, 2017, 8:1125, 12 pages.

Stavrou et al., "Retroviral transfer for a chimeric antigen receptor (CAR) to generate regulatory T cells for the treatment of autoimmunity and graft versus host disease," Human Gene Therapy, May 1, 2014, 25(5):A20, 1 page.

* cited by examiner

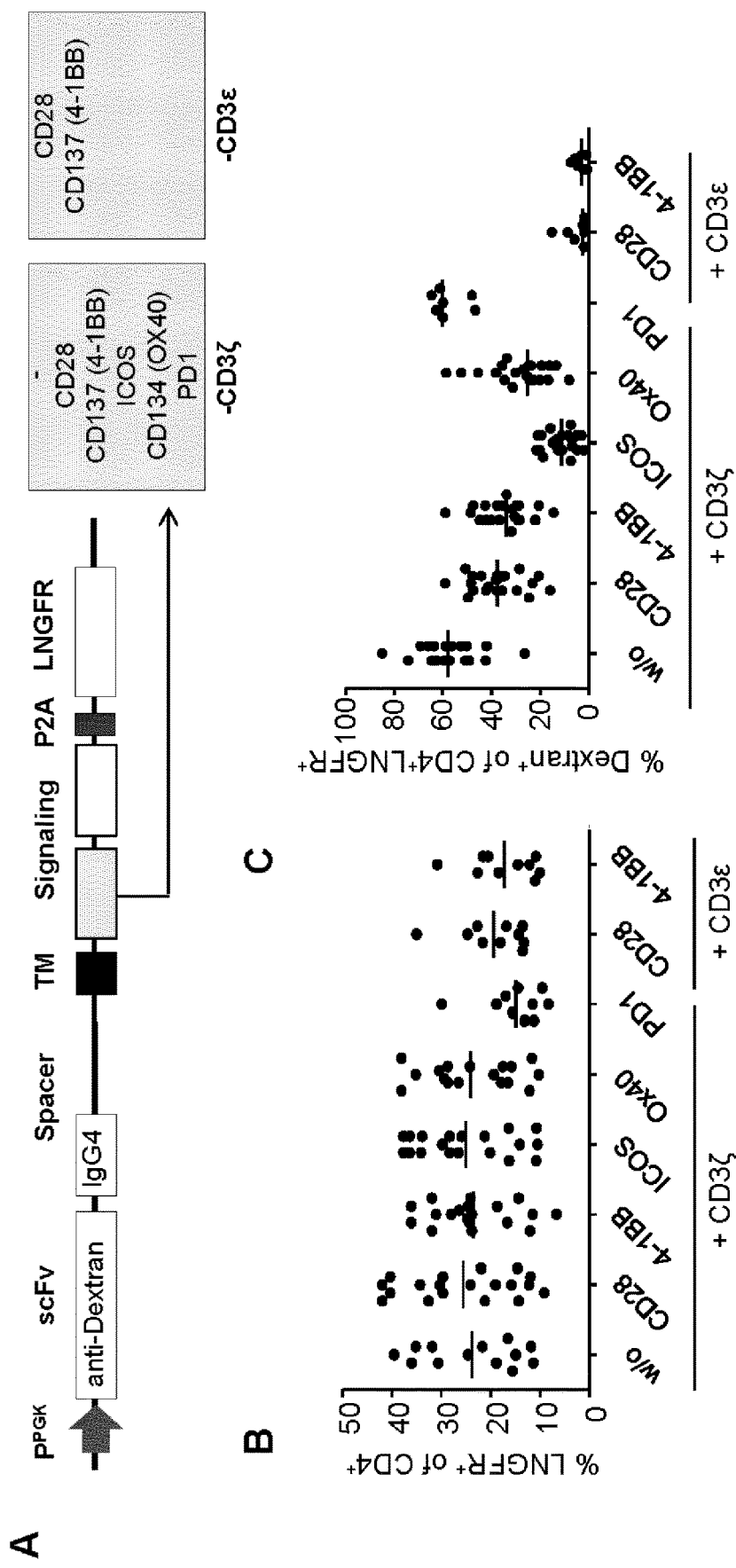
FIG 1 A-C

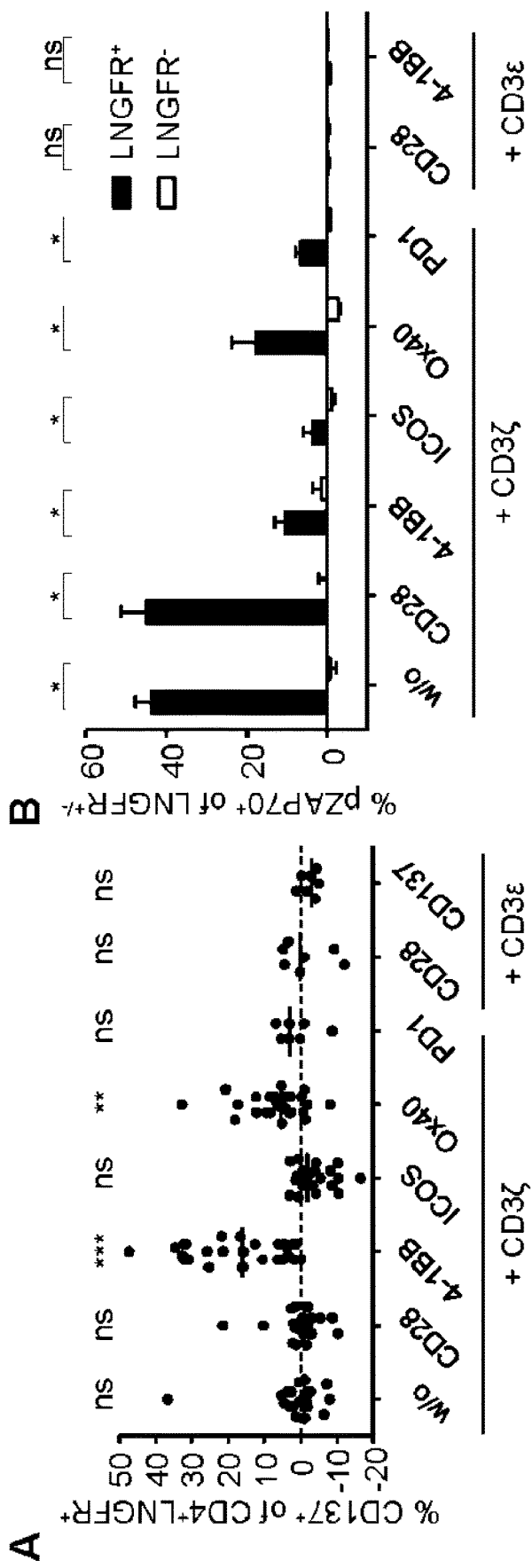
FIG 2 A, B

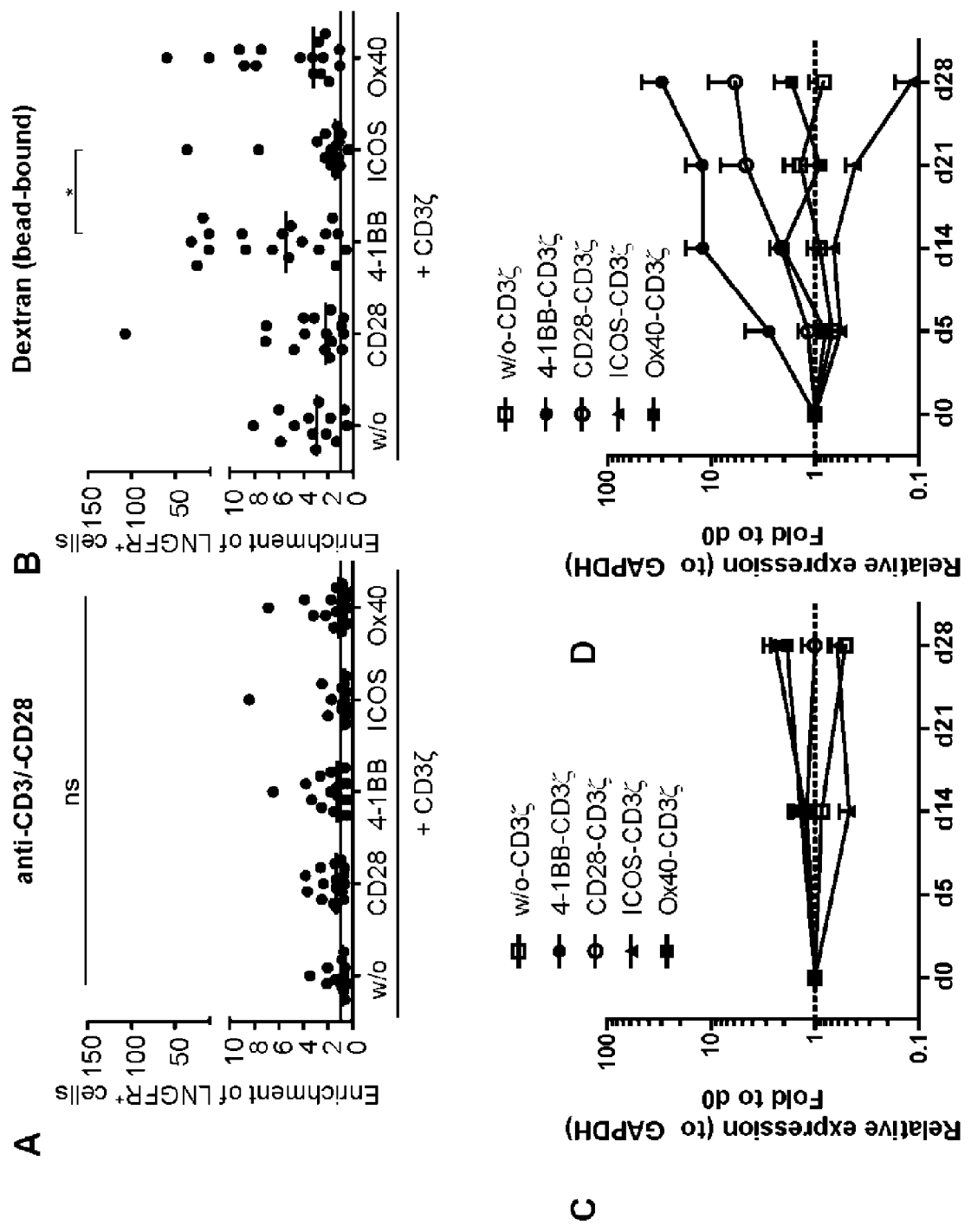
FIG 3 A-D

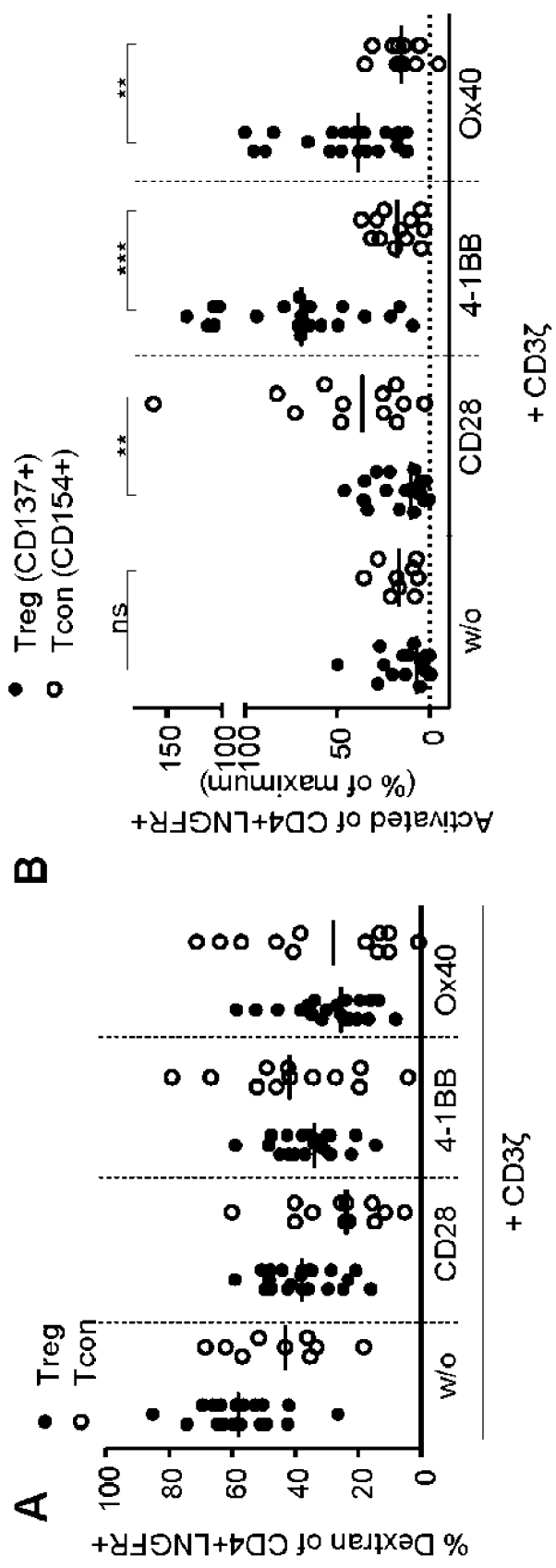
FIG 4 A, B

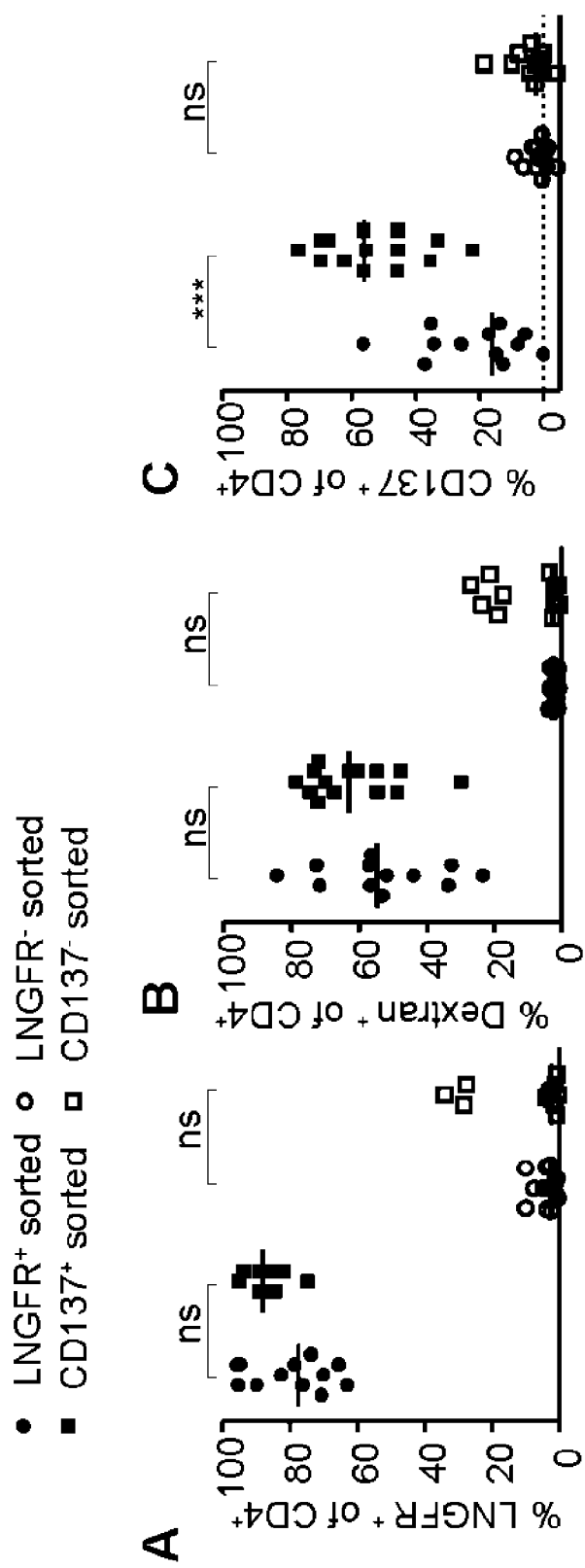
FIG 5 A-C

REGULATORY T CELL EXPRESSING A CHIMERIC ANTIGEN RECEPTOR

CROSS-REFERENCE TO RELATED APPLICATIONS

This application is a 371 U.S. National Stage entry of International Application No. PCT/EP2019/051143, filed on Jan. 17, 2019, which claims priority to European Patent Application No. 18152631.0, filed on Jan. 19, 2018, the entire contents of which are hereby incorporated by reference.

SEQUENCE LISTING

The instant application contains a Sequence Listing which has been submitted electronically in ASCII format and is hereby incorporated by reference in its entirety. Said ASCII copy, created on Jul. 10, 2020, is named Sequence_Listing.txt and is 2.37 kilobytes in size.

FIELD OF THE INVENTION

The present invention relates to the field of chimeric antigen receptors expressed in immune cells, in particular expressed in regulatory T cells.

BACKGROUND OF THE INVENTION

Conventional T cells (Tcon) can be manipulated to improve recognition and destruction of pathogens or tumors. Regulatory T cells (Tregs) comprise a subset of T cells with immunosuppressive function. Treg can be manipulated to prevent or treat autoimmunity, transplant rejection, allergy and chronic inflammatory diseases.

Chimeric antigen receptors (CARs) emerge as promising alternative for the generation of antigen-specific regulatory T cells (Tregs). Other than TCRs, CARs are artificial receptors that contain an antibody-type specificity that can bind surface antigens independent of MHC. The specific recognition of particular antigens by CAR-T cells is mediated by antibody-derived single chain variable fragments (scFv) with an extracellular spacer domain that are coupled via a transmembrane region to an intracellular TCR-derived signaling domain (Gross et al. 1989; Kuwana et al. 1987). In murine models, redirected CAR-Tregs reactive against myelin basic protein were able to ameliorate EAE (Mekala and Geiger 2005) and also CAR-Tregs specific for 2,4,6-trinitrophenol (TNP) or carcinoembryonic antigen (CEA) were successfully redirected to the colon where they were highly potent in suppressing colitis and development of its associated colorectal cancer (Blat et al. 2014; Elinav et al. 2009; Elinav et al. 2008). More recently, human CAR-Tregs were redirected toward HLA-A2 as commonly mismatched antigen in transplantation and have been shown to suppress xenogeneic GvHD (MacDonald et al. 2016; Noyan et al. 2017; Boardman et al. 2017). Furthermore, it has been demonstrated that CAR-Tregs have the potential to ameliorate allergic airway inflammation (Skuljec et al. 2017) and to prevent neutralizing immune responses against Factor VIII in mice (Yoon et al. 2017). McGovern et al (2017, Frontiers in Immunology, Vol. 8, Art. 1517 pp:1-6) reviews the current state of the art for Tregs expressing CARs.

To our knowledge the CAR constructs which have been used so far in Tregs have a CD28 co-stimulatory domain.

The identification of disease-relevant target antigens as prerequisite for the in vitro generation of antigen-specific Tregs remains a major challenge. Furthermore, functional assays for the analysis of CAR-Treg efficacy are limited due to a lack of markers that allow to specifically identify Treg and to test their specific activation requirements. This is important for the generation of optimal Treg CAR constructs and for generation of optimized Treg transplants, that is maximal CAR-related Treg functional activity and minimal contamination with effector T cells. Therefore, requirements for the activation and expansion of CAR-Tregs which can significantly differ from Tcons remain poorly understood.

There is a need in the art for regulatory T cells that express a CAR that may be used in treatment of a subject to protect or treat various immune-related disorders, such as autoimmunity, transplant rejection, allergy or chronic inflammatory diseases.

There is also a need in the art for the generation of highly purified and functionally optimized regulatory T cells that express a CAR that may be used in treatment of a subject to protect or treat said immune-related disorders.

SUMMARY OF THE INVENTION

It is crucial to have pure populations of Treg cells for therapeutic application and to be able to evaluate the effects of the CAR constructs on Treg function which might differ from the requirement of Tcon. However, in-vitro Treg populations are in general contaminated with Tcon cells and both populations are not easily separated from each other. To identify and isolate true activated Tregs from a sample comprising activated regulatory T cells and activated conventional T cells is a requirement for the analysis of effects of specific CAR constructs for Tregs in vitro and subsequently their functionality in vivo. Therefore the task to define the conditions for optimal CAR-mediated activation of Treg functional activity and to generate optimized CAR Treg has not been solved so far.

Such an identification and separation can be performed by the method as disclosed in EP2306191B1.

Here we show, by comparing different signaling domains, which are known to activate conventional T cells (Tcon) that surprisingly the use of the CD137 (4-1BB) co-stimulatory domain has a selective advantage for stimulating and expanding human regulatory T cells. This is important to optimize Treg function for adoptive Treg therapies.

FIG. 4 shows that surprisingly in-vitro Tregs are better activated via the CAR (as shown by CAR-ligand (antigen) induced expression of CD137 and expansion) when the CAR contains a CD137 (4-1BB) co-stimulatory signaling domain (herein also referred to as "CD137 CAR") as compared to a CAR with a CD28 co-stimulatory signaling domain (herein also referred to as "CD28 CAR"), whereas the opposite is true in Tcons. Thus the use of the CD137 CAR allows optimal stimulation of Tregs, which can be exploited for in vitro selection of activated Tregs following CAR-ligand (antigen) stimulation to generate highly purified CAR-ligand (antigen) reactive Treg. It is also expected that in-vivo CD137 CARs are better activated and expanded by the CAR ligand (antigen) than Tregs with CD28 CARs, since Treg function in vivo is strictly dependent on functional antigen-receptor activation, which is mimicked by the CAR constructs. The transduction or transfection of Tregs with a CAR as disclosed herein (a CAR with a CD137 co-stimulatory domain) allows the efficient in vitro activation of said engineered Treg cell via the CAR and provides a mean for the subsequent sorting of the activated Treg that express the CAR. This allows to generate a pure and functional Treg CAR population with benefits for the therapeutic use in a subject in need thereof because in vivo it will provide better safety due to less contaminants and improved therapeutic activity due to better CAR-ligand (antigen) induced activation and expansion. Furthermore in a specific embodiment of the invention the CD137 CAR provides improved in vivo activation of Treg in response to the soluble antigen such as dextran that is applied as external stimulus to the subject as compared to CD28 CAR or CARs with other signaling domains that do not react to such external stimuli, which in addition enhances the in vivo activity of the transferred Tregs, since it leads to the expansion of Tregs and increased Treg activity will also result in improved reactivity to the endogenous TCR or the Treg. In this way the CAR activation can be used to boost the natural regulatory or suppressive activity of the Treg to endogenous Treg antigens, without the need to know the specific Treg antigen targets.

The Tregs as disclosed herein are well suited for prevention or treatment of a subject suffering from immune-mediated diseases, such as autoimmunity, transplant rejection, allergy or chronic inflammatory diseases.

In one embodiment of the invention the CD137 CAR expressed in the Treg is specific for the exogenous soluble antigen dextran. The administration of dextran to a subject in need to be treated with said CAR specific for dextran may allow for a controlled and sustained immune response of the Treg cell expressing said CAR for prevention or treatment against autoimmunity, transplant rejection, allergy or chronic inflammatory diseases.

BRIEF DESCRIPTION OF THE DRAWINGS

FIG. 1: Generation of dextran-specific CAR-Tregs with different intracellular signaling domains. (A) Schematic diagram of CAR constructs with different signaling domains. (B) LNGFR expression on CD25-enriched Treg after lentiviral transduction is shown (n=10-19 from 3-6 different experiments). (C) Binding of soluble FITC Dextran is shown (n=7-21 from 2-7 independent experiments).

FIG. 2: Activation of dextran-specific CAR-Treg with different intracellular signaling domains. (A) CD137 expression was analysed after 6 h restimulation with bead-bound dextran, CD137 expression of unstimulated samples was subtracted (n=7-26, 2-8 different experiments were performed). (B) Phosphorylation of ZAP70 in LNGFR+ and LNGFR-Treg was analysed after 5 min incubation with soluble dextran (n=7, 2 independent experiments were performed).

FIG. 3: Expansion of dextran-specific CAR-Tregs with different intracellular signaling domains. Tregs were expanded in the presence of (A,C) anti-CD3/-CD28 or (B,D) bead-bound dextran. (A,B) Enrichment of LNGFR+ cells on d17 was calculated as the ratio of LNGFR-/LNGFR+ Treg on d0 x the ratio of LNGFR+/LNGFR- Treg on d17 (n=13-18 from 4-6 independent experiments). (C, D) Tregs with different signaling domains were pooled and relative expression of the different signaling domains was quantified by qPCR (n=7, 3 different experiments were performed).

FIG. 4: Comparison of different intracellular signaling domains in Tregs and Tcons. (A) Dextran binding of CAR-Tregs and CAR-Tcons is shown. (B) Analysis of activation of CAR-Tregs (CD137 expression) and CAR-Tcons (CD154 expression) after 6 h stimulation with bead-bound dextran; expression on LNGFR- Treg was subtracted for each sample as background and CD137 and CD154 expression were normalized to the percentage of dextran+ cells in each culture.

FIGS. 5: Isolation of CAR-Tregs by activation-induced CD137 expression. Unstimulated LNGFR+ Tregs or CD137+ LNGFR+Tregs after 6 h stimulation with bead-bound dextran were sorted and expanded with anti-CD3/−28 (LNGFR+ sorted) or without further stimulation (CD137+ sorted) for 14 days before staining of (A) LNGFR, (B) dextran and (C) CD137 expression after restimulation with bead-bound dextran (n=12, 4 independent experiments for LNGFR sorted; n=15, 5 different experiments for CD137 sorted).

DETAILED DESCRIPTION OF THE INVENTION

In a first aspect the present invention provides a regulatory T (Treg) cell expressing an antigen chimeric receptor (CAR) comprising
  a) at least one antigen binding domain,
  b) a transmembrane domain,
  c) a cytoplasmic signaling domain comprising at least one primary cytoplasmic signaling domain and at least the co-stimulatory signaling domain of CD137,
wherein said antigen binding domain specifically binds an antigen that is expressed on the surface of a target cell or a tag of a tagged polypeptide that binds to an antigen expressed on the surface of a target cell or a soluble antigen.

Said CAR, wherein said at least one primary cytoplasmic signaling domain may be CD3zeta. Said CAR, wherein said antigen binding domain may bind directly to an antigen that is expressed on the cell surface of a target cell. Said target cell may be a cell in a disease state that expresses a disease relevant autologous or allogeneic antigen. The disease may be an autoimmune disease, chronic inflammatory disease, allergy, transplant rejection, GvHD or an infection by virus, bacteria, parasite of a subject Alternatively said antigen binding domain of said CAR may bind a tag of a tagged polypeptide that binds to an antigen expressed on the surface of a target cell. Then said antigen binding domain of the CAR binds indirectly to the antigen that is expressed on the surface of the target cell. Such an adapter CAR approach is disclosed e.g. in U.S. Pat. No. 9,233,125B2. The tag may be a hapten such as biotin or FITC. The tagged polypeptide that binds to an antigen expressed on the surface of a cell may be an antibody or antigen binding fragment thereof.

Alternatively, and preferred, the antigen binding domain of said CAR may be specific for a soluble antigen, thereby allowing the activation of said Treg cell upon binding of said soluble antigen to said antigen binding domain of said CAR, preferentially without binding of said Treg cell to another cell.

Said soluble antigen may be an exogenous antigen that is not naturally present in the blood or tissue of a subject, preferentially a human to that said Treg cell expressing said CAR is applied to. More preferentially, said exogenous antigen that is not naturally present in the blood or tissue of a subject to that said Treg cell expressing said CAR is applied to has no preference to bind to another target in the subject than to the antigen binding domain of said CAR.

Said exogenous soluble antigen may be a non-disease causing antigen that evoke no harm to the subject when applied to said subject.

Said (exogenous) soluble antigen may be dextran.

Said antigen binding domain of said CAR may comprise the sequences of SEQ ID NO:1 and SEQ ID NO2. SEQ ID NO:1 represents a variable domain of the heavy chain of an immunoglobulin (VH) and SEQ ID NO:2 represents a variable region of a light chain of an immunoglobulin (VL).

Alternatively, the antigen (mono- or polyvalent) may be attached to biological surface, such as the surface of a cell or to tissue matrix compounds by use of specific attachment molecules. In this way the antigen can be directed in vivo to a specific surface, cell type or organ and the attachment to the surface also improves crosslinking of the CAR. This leads to a localized and improved Treg activation.

In an aspect the present invention provides a composition comprising
i) a regulatory T (Treg) cell expressing an antigen chimeric receptor (CAR) comprising
  a) at least one antigen binding domain,
  b) a transmembrane domain,
  c) a cytoplasmic signaling domain comprising at least one primary cytoplasmic signaling domain and at least the co-stimulatory signaling domain of CD137,
wherein said antigen binding domain specifically binds a tag of a tagged polypeptide that binds to an antigen expressed on the surface of a target cell or a soluble antigen,
ii) said tag polypeptide.

In a further aspect the present invention provides a Treg cell expressing a CAR as disclosed herein for use in the treatment or the prevention of an autoimmune disease, allergy, transplant rejection, graft versus host disease, chronic inflammatory diseases, such as inflammatory bowel diseases or a chronic infection by virus, bacteria, parasite of a subject.

In another aspect the present invention provides a composition comprising a population of Treg cells expressing a CAR as disclosed herein.

Said composition of a population of Treg cells expressing a CAR as disclosed herein may comprise at least 50%, 60%, 70%, 80%, 90%, 95% or 99% of Tregs cells., Said Tregs cells may be characterized by a CD25+CD127−FoxP3+ phenotype and/or a >80% demethylated TSDR (Treg Specific Demethylated Region) and/or the expression of CD137 and lack of CD154 expression following 5-7 hours of polyclonal stimulation, e.g. using anti-CD3/anti-CD28 molecules or pharmacological T cell activators, such as PMA/ionomycin.

Said composition, wherein said population of Treg cells expressing a CAR as disclosed herein may be a population of activated Tregs obtainable by the method for enrichment of activated Treg cells expressing a CAR as disclosed herein.

Said composition may be a pharmaceutical composition that optionally comprises a pharmaceutical acceptable carrier.

In a further aspect the present invention provides a combination of pharmaceutical compositions comprising
  a) a population of Treg cells expressing a CAR as disclosed herein together with a pharmaceutical acceptable carrier, and
  b) a soluble antigen as disclosed herein.

Said population of Treg cells expressing a CAR as disclosed herein may comprise at least 50%, 60%, 70%, 80%, 90%, 95% or 99% of Tregs cells. Said Tregs cells may be characterized by a CD25+CD127−FoxP3+ phenotype and/or a >80% demethylated TSDR and/or the expression of CD137 and lack of CD154 expression following 5-7 hours of polyclonal stimulation, e.g. using anti-CD3/anti-CD28 molecules or pharmacological T cell activators, such as PMA/ionomycin.

Said combination of pharmaceutical compositions for treatment or prevention of an autoimmune disease, allergy, transplant rejection, graft versus host disease, chronic inflammatory diseases, such as inflammatory bowel diseases or a chronic infection by virus, bacteria, parasite of a subject.

Said soluble antigen may be dextran.

Said combination of pharmaceutical compositions, wherein said population of Treg cells expressing a CAR as disclosed herein may be a population of activated Tregs obtainable by the method for enrichment of activated Treg cells expressing a CAR as disclosed herein.

In another aspect the present invention provides a method for enrichment of activated Treg cells expressing a CAR, wherein said CAR comprises
i) at least one antigen binding domain
ii) a transmembrane domain
iii) a cytoplasmic signaling domain comprising at least one primary cytoplasmic signaling domain and at least the co-stimulatory signaling domain of CD137, wherein said antigen binding domain specifically binds an antigen that is expressed on the surface of a target cell or a tag of a tagged polypeptide that binds to an antigen expressed on the surface of a target cell or a soluble antigen, the method comprising
  a) providing a sample comprising regulatory T cells
  b) genetically modifying said regulatory T cells of said sample to express said CAR
  c) activating said genetically modified regulatory T cells via contacting with the antigen that is bound by the antigen binding domain of said CAR for 6-16 hours
  d) isolation of the activated Treg cells of step c) by
    α) contacting the cells of step c) with
      I) a molecule binding CD154 and depletion of CD154+ T-cells; or
      II) a molecule binding a marker for regulatory T-cells or for activated regulatory T cells and positive selection of the cells that bind to said binding molecule, and
    β) contacting
      I) the cells of step α)I) with a molecule binding a marker for regulatory T-cells or for activated regulatory T-cells and positive selection of the cells that bind to said binding molecule, thereby obtaining a population of activated regulatory T-cells expressing said CAR; or
      II) the cells of step α)II) with a molecule binding CD154 and depletion of CD154+ T-cells, thereby obtaining a population of activated regulatory T-cells expressing said CAR.

Optionally said method may also comprise the step of expanding the genetically modified regulatory T cells after step b) and before step c).

Said CAR and said antigen(s) of the method may have the features and characteristics of the CAR and antigen(s) as already described above and disclosed herein. All variants and embodiments disclosed above for the CAR and the antigens as disclosed herein may also apply for said method.

Said method, wherein the marker for regulatory T-cells is selected from the group of markers CD25 and GITR; and wherein the marker for activated regulatory T-cells is selected from the group of markers CD137, latent TGF-beta (LAP), GARP (LRRC32) and CD121a/b. Said method, wherein the molecules binding CD154 or a marker for regulatory T cells or for activated regulatory T-cells may be antibodies or antigen binding fragments thereof.

Said method, wherein said genetically modified regulatory T cells (step c) are expanded in the presence of anti-CD3/-CD28 and/or the antigen that binds to the antigen binding domain of the CAR as disclosed herein and addition of appropriate growth factors, such as IL-2.

Said method, wherein the isolation (separation) is performed using flow-cytometry or magnetic cell sorting.

Said method, wherein the molecule binding CD154 and/or the molecule binding a marker for regulatory T-cells or for activated regulatory T-cells are coupled to a fluorescent dye, a hapten and/or to a magnetic particle.

Said method, wherein the sample that is provided (step a) is derived from whole blood, PBMC, cord blood, lymph node tissue, bone marrow, or leukapheresis.

Said method, wherein the genetic modification of said regulatory T cells of said sample to express said CAR (step b) may be performed by methods well known in the art (e.g. viral-based systems, physical methods, biological methods, chemical methods).

Said genetic modification of the Treg cells may be performed by transduction, transfection or electroporation. Preferably, transduction is performed with lentiviruses, gamma-, alpha-retroviruses or adenoviruses or with electroporation or transfection by nucleic acids (DNA, mRNA, miRNA, antagomirs, ODNs), proteins, site-specific nucleases (zinc finger nucleases, TALENs, CRISP/R), self replicating RNA viruses (e.g. equine encephalopathy virus) or integration-deficient lentiviral vectors. More preferentially, said genetic modification of Treg cells may be performed by transducing said cells with lentiviral vectors.

Said method, wherein the enriched population of activated Treg cells expressing said CAR comprise at least 50%, 60%, 70%, 80%, 90%, 95% or 99% of Tregs cells. Said Tregs cells are characterized by a CD25+CD127−FoxP3+ phenotype and/or a >80% demethylated TSDR and/or the expression of CD137 and lack of CD154 expression following 5-7 hours of polyclonal stimulation, e.g. using CD3/CD28 or pharmacological T cell activators, such as PMA/ionomycin.

Said method, wherein the method may be performed in a closed system.

Said method, wherein the method is an automated method in a closed system.

The present invention also provides the use of a CD137 CAR expressed in a Treg cell to select from a variety of CARs (at least two) those CARs which allow best activation of Tregs by using at least two CARs comprising a CD137 signaling domain (CD137 CAR), but differing in at least one other component of the CAR and compare their capability to activate a Treg expressing said CAR, e.g. by contacting the CAR expressing Treg with the CAR ligand (antigen) and measuring and comparing the extent of induction of CD137 surface expression or another Treg activation marker known to be expressed after activation of Treg cells.

Therefore, in a further aspect, the present invention provides the use of a CAR expressed in a regulatory T (Treg) cell for analyzing the activation efficiency of a Treg cell, wherein said CAR comprises
 a) at least one antigen binding domain,
 b) a transmembrane domain,
 c) a cytoplasmic signaling domain comprising at least one primary cytoplasmic signaling domain and at least the co-stimulatory signaling domain of CD137,
wherein said antigen binding domain specifically binds an antigen that is expressed on the surface of a target cell or a tag of a tagged polypeptide that binds to an antigen expressed on the surface of a target cell or a soluble antigen.

In a further aspect, the present invention provides a method for analyzing (comparing) the activation efficiency of at least two Treg cells, wherein an at least first Treg cell expresses a first chimeric antigen receptor (CAR) comprising
 a) at least one antigen binding domain,
 b) a transmembrane domain,
 c) a cytoplasmic signaling domain comprising at least one primary cytoplasmic signaling domain and at least the co-stimulatory signaling domain of CD137,
wherein an at least second Treg cell expresses a second CAR that is different from said first CAR in at least one domain of the first CAR but expresses the co-stimulatory signaling domain of CD137 and,
wherein said antigen binding domains of said at least first CAR and of said at least second CAR specifically bind an antigen that is expressed on the surface of a target cell or a tag of a tagged polypeptide that binds to an antigen expressed on the surface of a target cell or a soluble antigen, the method comprising
 a) providing a sample comprising regulatory T cells
 b) genetically modifying said at least first Treg cell to express said at least first CAR and genetically modifying said at least second Treg cell to express said at least second CAR
 c) activating said genetically modified at least first Treg cell and at least second Treg cell via contacting with the antigen that is bound by the antigen binding domains of said at least first CAR and said at least second CAR for 6-16 hours
 d) measuring the expression level of a Treg activation marker of said at least first Treg cell and said at least second Treg cell, wherein a different expression level indicates a different activation efficiency of said at least first CAR and said at least second CAR in Treg cells.

Comparing the strength of activation induced by contacting the CARs with their ligand (antigen) allows the optimization of a CAR for use in Treg by selecting the CAR with the strongest activation capability.

The term "a domain of the CAR" as used herein in the context of comparing the activation efficiency of at least two CARs in a Treg cell refers to any domain that may be used in a functional CAR, such domains may be e.g. the extracellular domain, the transmembrane domain and the intracellular domain of a CAR. The extracellular domains may be at least one antigen binding domain, a linker such as (G4/S)3 and/or a spacer/hinge such as CD8 hinge. The intracellular domain may be at least one stimulatory signaling domain, and/or at least one co-stimulatory signaling domain. The difference that may exist between the at least two CARs that are compared with each other may comprise the modification of a domain which may be functionally relevant in a CAR, i.e. influencing stability, expression level, antigen-binding or ligand (antigen) induced CAR-mediated signaling cascade, which eventually affects CAR-mediated Treg activation. The term "modification" comprises for example the complete or partial substitution or the deletion of such a domain, the positioning of the domain within the CAR or merely the modification of the amino acid sequences of the domain, i.e. exchange, insertion, removal, etc. of at least one amino acid of such a domain.

The terms "Treg activation" or "activation efficiency in Treg cells" mean changes of the Treg gene expression pattern or functional changes induced by antigen receptor triggering. Treg activation is required in vivo to allow the Treg to exert their physiological function, e.g. suppression of inappropriate or pathological immune reactions, such as allergy, autoimmunity, graft versus host disease and transplant rejection, IBD and other chronic inflammatory diseases. There are various parameters and methods known in the field to measure Treg activation, such as expression of activation markers. Said Treg activation marker may be selected from the group of markers CD137, latent TGF-beta (LAP), GARP (LRRC32), CD121a/b, or IL-10. Or functional assays such as the suppression of responder T cell proliferation by coculture with activated Treg. One particular parameter of Treg activation is induction of CD137 but simultaneous absence of CD154 after 4-7 hours of stimulation, which is a highly specific Treg activation signature. This can be measured by standard technologies known to experts in the field, such as fluorescent antibody staining and flow-cytometry. Quantitative differences in Treg activation can be either the amount of CD137 expressed on a single cell or the number or proportion of cells which is induced to express the marker.

Said first CAR and said antigen(s) of the method may have the features and characteristics of the CAR and antigen(s) as already described above and disclosed herein. All variants and embodiments disclosed above for the CAR and the antigens as disclosed herein may also apply for said method.

Said second CAR may be a variant of the first CAR having at least one modification compared to said first CAR that may affect e.g. the antigen binding characteristics and and/or the signal transduction capabilities resulting in an altered Treg cell activation characteristics of said second CAR compared to said first CAR.

The modification of said second CAR compared to said first CAR may be e.g. a different spacer, a different antigen binding domain specific for the same antigen, a different transmembrane domain and/or a different signaling domain Said method, wherein the sample that is provided (step a) may be derived from whole blood, PBMC, cord blood, lymph node tissue, bone marrow, or leukapheresis.

Said method, wherein the genetic modification of said regulatory T cells of said sample to express said CAR (step b) may be performed by methods well known in the art (e.g. viral-based systems, physical methods, biological methods, chemical methods).

Said genetic modification of the Treg cells may be performed by transduction, transfection or electroporation. Preferably, transduction is performed with lentiviruses, gamma-, alpha-retroviruses or adenoviruses or with electroporation or transfection by nucleic acids (DNA, mRNA, miRNA, antagomirs, ODNs), proteins, site-specific nucleases (zinc finger nucleases, TALENs, CRISP/R), self replicating RNA viruses (e.g. equine encephalopathy virus) or integration-deficient lentiviral vectors. More preferably, said genetic modification of Treg cells may be performed by transducing said cells with lentiviral vectors.

The present invention also provides a method to test various antigen formulations to induce Treg activation via contacting said antigen with a CD137 CAR. For example the capacity of a first antigen sample to activate a CD137 CAR expressing Treg with an at least second antigen sample that is different from the first antigen sample, via contacting the antigen sample with a Treg expressing a CAR with the antigen binding domain and comparing the Treg activation induced by said various antigen samples.

Therefore, in a further aspect, the present invention provides a method for analyzing (comparing) the activation efficiency of a first antigen sample to activate a CAR expressed in a Treg cell with a second antigen sample that is different from the first antigen sample, the CAR comprising
a) at least one antigen binding domain,
b) a transmembrane domain,
c) a cytoplasmic signaling domain comprising at least one primary cytoplasmic signaling domain and at least the co-stimulatory signaling domain of CD137, wherein said antigen binding domain specifically binds the antigen of said first antigen sample that is expressed on the surface of a target cell or a tag of a tagged polypeptide that binds to an antigen expressed on the surface of a target cell or a soluble antigen,
the method comprising
a) providing a sample comprising regulatory T cells
b) genetically modifying said Treg cell to express said CAR
c) activating said genetically modified Treg cell via contacting the antigen binding domain of said CAR with said first antigen sample for 6-16 hours, and activating said genetically modified Treg cell via contacting the antigen binding domain of said CAR with said second antigen sample for 6-16 hours
d) measuring the Treg activation of said Treg cell that was contacted with said first antigen sample and of said Treg cell that was contacted with the second antigen sample, wherein a different activation level indicates a different efficiency of said first antigen sample and said second antigen sample to activate the functional activity of said CAR expressed in Treg cells.

Said first antigen sample and said second antigen sample may differ e.g. in the formulation of the antigen, e.g. soluble form, monomers versus multimerized antigens, antigen attached to various carriers, e.g. large surface such as culture dishes, microbeads of variable size, e.g. 50 nm-50 μm but not restricted to that, or biocompatible macromolecular matrices, such as dextran, or other polysaccharides, or different antigens that can be bound by the same antigen binding domain of the CAR, but e.g. with different affinity or with different conformational changes induced in the CAR etc.

The DNA or RNA construct(s) (nucleic acid molecule(s)) encoding the CAR as disclosed herein may be transfected or transduced into a host cell by methods well known in the art (e.g. viral-based systems including retrovirus and lentivirus, physical methods including electoporation, biological methods, chemical methods). Regardless the methods used to integrate, preferentially stably integrate, the DNA encoding the CAR as disclosed herein in the host cell, as a result the host cell expresses the CAR as disclosed herein.

Alternatively, the nucleic acid sequences may be produced synthetically.

An engineered cell expressing the antigen binding receptor as disclosed herein may be isolated (enriched or separated) after the transfection/transduction process for generating such an engineered cell from non-transfected/transduced cells by methods well known in the art, e.g. fluorescent based separating technologies such as FACS® or magnetic cell separation methods such as MACS® (Miltenyi Biotec GmbH).

Generally, the cells such as immune cells, preferentially T cells for generating engineered cells expressing the antigen binding receptor as disclosed herein may be obtained from a subject. Cells such as immune cells, preferentially T cells, can be obtained from a variety of sources such as whole blood, peripheral blood mononuclear cells (PBMCs), bone marrow, lymph node tissue, cord blood, thymus tissue or other tissues containing T cells. For enrichment of these cells methods well known in the art can be used such as centrifugation through a Ficoll™ or PERCOLL™ gradient or positive/negative selection techniques such as fluorescent sorting (e.g. FACSsort) or magnetic sorting (e.g. MACS®).

Exemplary, Tregs of a blood or tissue sample of a subject are magnetically labelled, for example with a magnetic bead coupled to antibodies specific for CD25, washed, magnetically enriched and collected. Then these Tregs may be engineered to express the antigen binding receptor as disclosed herein on their cell surface.

In one embodiment of the invention the isolated/enriched engineered cell such as immune cells, preferentially Treg cells expressing the antigen binding receptor as disclosed herein may be activated prior or after genetic modification and expanded to increase the number of engineered cells using methods well known in the art, for example polyclonal stimulation of Tregs with the Treg Expansion Kit (Miltenyi Biotec) that consists of a micron-sized particle conjugated to CD3 and CD28 binding antibodies in the presence of suitable growth factors such as IL-2. Preferentially, said number of engineered cells such as immune cells, e.g. T cells, may be increased to a therapeutically effective amount.

The genetically modified Treg cells expressing the CAR as disclosed herein may be generated in an automated process in a closed system. In one embodiment of the invention a process for the generation of genetically modified Tregs expressing the CAR as disclosed herein may comprise e.g. the steps:
a) providing a sample comprising regulatory T cells
b) genetically modifying said regulatory T cells of said sample to express said CAR
c) optionally expanding the genetically modified regulatory T cells
d) activating said expanded genetically modified regulatory T cells via contacting with the CAR ligand for 6-16 hours
e) isolation of the activated Treg cells of step d) by
α) contacting the cells of step d) with
I) a molecule binding CD154 and depletion of CD154+ T-cells; or
II) a molecule binding a marker for regulatory T-cells or for activated regulatory T cells such as CD137 and positive selection of the cells that bind to said binding molecule, and
β) contacting
I) the cells of step α)I) with a molecule binding a marker for regulatory T-cells or for activated regulatory T-cells such as CD137 and positive selection of the cells that bind to said binding molecule, thereby obtaining a population of activated regulatory T-cells expressing said CAR; or
II) the cells of step α)II) with a molecule binding CD154 and depletion of CD154+ T-cells, thereby obtaining a population of activated regulatory T-cells expressing said CAR.

All or some these steps may be performed automatically in a closed system, preferably in a closed and sterile system.

The process is especially suited for preparing gene modified Treg cells, wherein the enriched Treg cells are gene-modified by using viral and/or non-viral vectors.

Any of these steps may be multiplied, omitted or may occur in a different order.

As a closed system for cell modification, the fully automated cell processing device CliniMACS Prodigy® and associated tubing sets (Miltenyi Biotec GmbH, Germany) may be used (WO2009/072003). This closed system meets the requirements of GMP-grade processing of almost any kind of cellular products and may allow reducing clean room requirements, improve technology transfer and harmonization of cell manufacturing processes.

In one embodiment of the invention, the engineered Tregs expressing the CAR as disclosed herein may be for use in the treatment in a subject suffering from a disorder such as autoimmunity, transplant rejection, allergy or chronic inflammatory diseases.

Tregs may be isolated from a subject, preferentially a human or established immune cell lines may be used. The subject may suffer from said disorder or may be a healthy subject. These Treg cells are genetically modified in vitro to express the CAR as disclosed herein. These engineered Treg cells may be activated and expanded in vitro to a therapeutically effective population of cells expressing the CAR as disclosed herein and they may be further enriched before or after the modification to more purity by the method as disclosed herein. In cellular therapy these engineered Treg cells may be infused to a recipient in need thereof as a pharmaceutical composition (or a formulation of a therapeutically effective population of cells expressing the CAR as disclosed herein), in addition to a second pharmaceutical composition, the soluble antigen that has the function of an external stimulus of the Treg cells. The infused Treg cells in the recipient may be able to suppress inflammatory immune reactions of the subject or at least reduce the effects and/or symptoms of said disorder under treatment. The recipient may be the same subject from which the cells were obtained (autologous cell therapy) or may be from another subject of the same species (allogeneic cell therapy).

Populations of Treg cells expressing the CAR as disclosed herein may be formulated for administered to a subject using techniques known to the skilled artisan.

Formulations comprising therapeutically effective population(s) of Treg cells expressing the CAR as disclosed herein may include pharmaceutically acceptable excipient(s) (carrier or diluents). Excipients included in the formulations will have different purposes depending, for example, on the nature of the antigen binding domain of the CAR as disclosed herein. Examples of generally used excipients include, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents.

A formulation of a therapeutically effective population(s) of Treg cells expressing the CAR as disclosed herein may include one population of Treg cells expressing the CAR as disclosed herein, or more than one population of cells expressing the CAR as disclosed herein. The different populations of Treg cells expressing the CAR as disclosed herein may e.g. vary based on the identity of the antigen binding domain and/or the identity of the activation domain of the used CAR.

The formulations comprising therapeutically effective population(s) of Treg cells expressing the CAR as disclosed herein may be administered to a subject using modes and techniques known to the skilled artisan. Exemplary modes include, but are not limited to, intravenous injection. Other modes include, without limitation, intratumoral, intradermal, subcutaneous (s.c, s.q., sub-Q, Hypo), intramuscular (i.m.), intraperitoneal (i.p.), intra-arterial, intramedulary, intracardiac, intra-articular (joint), intrasynovial (joint fluid area), intracranial, intraspinal, and intrathecal (spinal fluids).

The formulations comprising therapeutically effective population(s) of Treg cells expressing the CAR as disclosed herein that are administered to a subject comprise a number of Treg cells expressing the CAR as disclosed that is effective for the treatment of the specific indication or disorder.

In general, formulations may be administered that comprise between about $1 \times 10^4$ and about $1 \times 10^{10}$ Treg cells expressing the CAR as disclosed herein. In most cases, the formulation may comprise between about $1 \times 10^5$ and about $1 \times 10^9$ Treg cells expressing the CAR as disclosed herein, from about 5×10$^5$ to about 5×10$^8$ Treg cells expressing the CAR as disclosed herein, or from about 1×10$^6$ to about 1×10$^7$ Treg cells expressing the CAR as disclosed herein. However, the number of Treg cells expressing the CAR as disclosed herein administered to a subject may vary between wide limits, depending upon the location, source, identity, extent and severity of the disorder, the age and condition of the individual to be treated, etc. A physician may ultimately determine appropriate dosages to be used.

The soluble antigen such as dextran may be formulated for administered to a subject using techniques known to the skilled artisan. Formulations of the soluble antigens such as dextran may include pharmaceutically acceptable excipient(s) (carriers or diluents). Excipients included in the formulations will have different purposes depending, for example, on the nature of the soluble antigen and the mode of administration. Examples of generally used excipients include, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents.

A formulation of soluble antigens may include one type of soluble antigen, or more than one type of soluble antigen.

The soluble antigen(s) such as dextran may be administered to a subject using modes and techniques known to the skilled artisan. Exemplary modes include, but are not limited to, intravenous, intraperitoneal, and intratumoral injection. Other modes include, without limitation, intradermal, subcutaneous (s.c, s.q., sub-Q, Hypo), intramuscular (i.m.), intra-arterial, intramedulary, intracardiac, intra-articular (joint), intrasynovial (joint fluid area), intracranial, intraspinal, and intrathecal (spinal fluids).

Formulations comprising the soluble antigen(s) such as dextran are administered to a subject in an amount which is effective for treating the specific indication or disorder. In general, formulations comprising at least about 1 μg/kg to about 100 mg/kg body weight of the soluble antigen such as dextran may be administered to a subject in need of treatment. In most cases, the dosage may be from about 100 μg/kg to about 10 mg/kg body weight of the soluble antigen such as dextran daily or weekly or monthly, taking into account the routes of administration, symptoms, etc. However, the amount of soluble antigen(s) such as dextran in formulations administered to a subject may vary between wide limits, depending upon the location, source, identity, extent and severity of the disorder, the age and condition of the individual to be treated, etc. A physician may ultimately determine appropriate dosages to be used.

All definitions, characteristics and embodiments defined herein with regard to an aspect of the invention, e.g. the first aspect of the invention, also apply mutatis mutandis in the context of the other aspects of the invention as disclosed herein.

Definitions

Unless defined otherwise, technical and scientific terms used herein have the same meaning as commonly understood by one of ordinary skill in the art to which this invention belongs.

In general, a CAR may comprise an extracellular domain (extracellular part) comprising the antigen binding domain, a transmembrane domain and a cytoplasmic signaling domain (intracellular signaling domain). The extracellular domain may be linked to the transmembrane domain by a linker. The extracellular domain may also comprise a signal peptide. In some embodiments of the invention the antigen binding domain of a CAR binds a hapten that is coupled to a polypeptide ("haptenylated" or "tagged" polypeptide), wherein the polypeptide may bind to a disease-associated antigen such as an autoantigen or an antigen derived from harmless exogenous substances, e.g. microbiota, airborne particles, such as plant pollen, fungal spores. Such a CAR may be also named "anti-tag" CAR as disclosed e.g. in U.S. Pat. No. 9,233,125B2. In other embodiments of the invention, the extracellular part of the CAR may comprise a linker/label epitope (LLE) binding domain as antigen binding domain that binds to a linker/label epitope (LLE) that is part of a TCBM. Such a CAR may be named anti-LLE CAR as disclosed in the European patent application no. EP16196487.9. Both types of CARs are universal and/or adaptable CAR. Both the hapten(s) and the LLE are "tags" that are coupled directly or indirectly to a polypeptide (the tagged polypeptide), wherein the polypeptide may bind to a disease associated antigen such as an autoantigen expressed on the (cell) surface of a target cell or an antigen derived from harmless exogenous substances, e.g. microbiota, airborne particles, such as plant pollen, fungal spores. In other embodiments of the invention the antigen binding domain of the CAR binds to a soluble antigen as disclosed herein.

A "signal peptide" refers to a peptide sequence that directs the transport and localization of the protein within a cell, e.g. to a certain cell organelle (such as the endoplasmic reticulum) and/or the cell surface.

Generally, an "antigen binding domain" refers to the region of the CAR that specifically binds to an antigen, e.g. to a soluble antigen. The CARs of the invention may comprise one or more antigen binding domains. Generally, the targeting regions on the CAR are extracellular. The antigen binding domain may comprise an antibody or an antigen binding fragment thereof. The antigen binding domain may comprise, for example, full length heavy chain, Fab fragments, single chain Fv (scFv) fragments, divalent single chain antibodies or diabodies. Any molecule that binds specifically to a given antigen such as affibodies or ligand binding domains from naturally occurring receptors may be used as an antigen binding domain. Often the antigen binding domain is a scFv. Normally, in a scFv the variable regions of an immunoglobulin heavy chain and light chain are fused by a flexible linker to form a scFv. Such a linker may be for example the "(G$_4$/S)$_3$-linker".

In some instances, it is beneficial for the antigen binding domain to be derived from the same species in which the CAR will be used in. For example, when it is planned to use it therapeutically in humans, it may be beneficial for the antigen binding domain of the CAR to comprise a human or humanized antibody or antigen binding fragment thereof. Human or humanized antibodies or antigen binding fragments thereof can be made by a variety of methods well known in the art.

"Spacer" or "hinge" as used herein refers to the hydrophilic region which is between the antigen binding domain and the transmembrane domain. The CARs of the invention may comprise an extracellular spacer domain but is it also possible to leave out such a spacer. The spacer may include e.g. Fc fragments of antibodies or fragments thereof, hinge regions of antibodies or fragments thereof, CH2 or CH3 regions of antibodies, accessory proteins, artificial spacer sequences or combinations thereof. A prominent example of a spacer is the CD8alpha hinge. The transmembrane domain of the CAR may be derived from any desired natural or synthetic source for such domain. When the source is natural the domain may be derived from any membrane-bound or transmembrane protein. The transmembrane domain may be derived for example from CD8alpha or CD28. When the key signaling and antigen recognition modules (domains) are on two (or even more) polypeptides then the CAR may have two (or more) transmembrane domains. The splitting key signaling and antigen recognition modules enable for a small molecule-dependent, titratable and reversible control over CAR cell expression (Wu et al, 2015, Science 350: 293-303) due to small molecule-dependent heterodimerizing domains in each polypeptide of the CAR.

The cytoplasmic signaling domain (or the intracellular signaling domain) of the CAR is responsible for activation of at least one of the normal effector functions of the immune cell in which the CAR is expressed. "Effector function" means a specialized function of a cell, e.g. in a Treg an effector function may be suppressive activity or regulatory activity including the secretion of immunosuppressive cytokines, such IL-10, IL-35, TGF-beta or expression of inhibitory molecules, such as TIGIT, CTLA4, competitive cytokine receptors such as IL-2 receptor. The intracellular signaling domain refers to the part of a protein which transduces the effector function signal and directs the cell expressing the CAR to perform a specialized function. The intracellular signaling domain may include any complete, mutated or truncated part of the intracellular signaling domain of a given protein sufficient to transduce a signal which initiates or blocks immune cell effector functions.

Prominent examples of intracellular signaling domains for use in the CARs include the cytoplasmic signaling sequences of the T cell receptor (TCR) and co-receptors that initiate signal transduction following antigen receptor engagement.

Generally, T cell activation can be mediated by two distinct classes of cytoplasmic signaling sequences, firstly those that initiate antigen-dependent primary activation through the TCR (primary cytoplasmic signaling sequences, primary cytoplasmic signaling domain) and secondly those that act in an antigen-independent manner to provide a secondary or co-stimulatory signal (secondary cytoplasmic signaling sequences, co-stimulatory signaling domain). Therefore, an intracellular signaling domain of a CAR may comprise one or more primary cytoplasmic signaling domains and/or one or more secondary cytoplasmic signaling domains.

Primary cytoplasmic signaling domains that act in a stimulatory manner may contain ITAMs (immunoreceptor tyrosine-based activation motifs).

Examples of ITAM containing primary cytoplasmic signaling domains often used in CARs are that those derived from TCRζ (CD3ζ), FcRgamma, FcRbeta, CD3gamma, CD3delta, CD3epsilon, CD5, CD22, CD79a, CD79b, and CD66d. Most prominent is sequence derived from CD3ζ.

The cytoplasmic domain of the CAR may be designed to comprise the CD3ζ signaling domain by itself or combined with any other desired cytoplasmic domain(s). The cytoplasmic domain of the CAR can comprise a CD3ζ chain portion and a co-stimulatory signaling region (domain). The co-stimulatory signaling region refers to a part of the CAR comprising the intracellular domain of a co-stimulatory molecule. A co-stimulatory molecule is a cell surface molecule other than an antigen receptor or their ligands that is required for an efficient response of lymphocytes to an antigen. Examples for a co-stimulatory molecule are CD27, CD28, 4-1BB (CD137), OX40, CD30, CD40, PD-1, ICOS, lymphocyte function-associated antigen-1 (LFA-1), CD2, CD7, LIGHT, NKG2C, B7-H3.

The cytoplasmic signaling sequences within the cytoplasmic signaling part of the CAR may be linked to each other with or without a linker in a random or specified order. A short oligo- or polypeptide linker, which is preferably between 2 and 10 amino acids in length, may form the linkage. A prominent linker is the glycine-serine doublet.

As an example, the cytoplasmic domain may comprise the signaling domain of CD3ζ and the signaling domain of CD28. In another example the cytoplasmic domain may comprise the signaling domain of CD3ζ and the signaling domain of CD137. In a further example, the cytoplasmic domain may comprise the signaling domain of CD3ζ, the signaling domain of CD28, and the signaling domain of CD137.

The term "CD137 CAR" as used herein means that the CAR comprises at least a CD137 costimulatory signaling domain, in addition to at least a primary cytoplasmic signaling domain. The term "CD28 CAR" as used herein means that the CAR comprises at least a CD28 costimulatory signaling domain, in addition to at least a primary cytoplasmic signaling domain. As aforementioned either the extracellular part or the transmembrane domain or the cytoplasmic domain of a CAR may also comprise a heterodimerizing domain for the aim of splitting key signaling and antigen recognition modules of the CAR.

The CAR may be further modified to include on the level of the nucleic acid encoding the CAR one or more operative elements to eliminate CAR-T cells or Treg cells by virtue of a suicide switch. The suicide switch can include, for example, an apoptosis inducing signaling cascade or a drug that induces cell death. In one embodiment, the nucleic acid expressing and encoding the CAR can be further modified to express an enzyme such thymidine kinase (TK) or cytosine deaminase (CD).

The CARs of the present invention may be designed to comprise any portion or part of the above-mentioned domains as described herein in any order and/or combination resulting in a functional CAR, i.e. a CAR that mediated an immune effector response of the immune effector cell that expresses the CAR but comprises at least a CD137 co-stimulatory domain.

The term "antibody" as used herein is used in the broadest sense to cover the various forms of antibody structures including but not being limited to monoclonal and polyclonal antibodies (including full length antibodies), multispecific antibodies (e.g. bispecific antibodies), antibody fragments, i.e. antigen binding fragments of an antibody, immunoadhesins and antibody-immunoadhesin chimeras, that specifically recognize (i.e. bind) a target antigen. "Antibody fragments" comprise a portion of a full length antibody, preferably the variable domain thereof, or at least the antigen binding site thereof ("an antigen binding fragment of an antibody"). Examples of antibody fragments include Fab (fragment antigen binding), scFv (single chain fragment variable), single domain antibodies, diabodies, dsFv, Fab', diabodies, single-chain antibody molecules, and multispecific antibodies formed from antibody fragments.

As used herein, the term "antigen" is intended to include substances that bind to or evoke the production of one or more antibodies and may comprise, but is not limited to, proteins, peptides, polypeptides, oligopeptides, lipids, carbohydrates such as dextran, haptens and combinations thereof, for example a glycosylated protein or a glycolipid.

The term antigen may refer to an antigen expressed on a cell surface of a target cell. But the term may also refer to an antigen that is not expressed or present on the surface of a cell, e.g. in a subject that may be treated with engineered Tregs expressing a CAR as disclosed herein. Then the antigen is herein referred to as "soluble antigen". The terms "soluble antigen" and "free antigen" as used herein can be used interchangeably and mean that the soluble antigen that can be bound by the antigen binding domain of the CAR as disclosed herein is not naturally expressed or present on the surface of a cell of a subject, preferentially a human, when a Treg expressing said CAR is applied to said subject. Preferentially, the soluble antigen is not present in the blood or tissue of a subject to that said Treg cell expressing said CAR is applied to. More preferentially it has also no specific affinity or preference to bind to another molecule in the subject than to the antigen binding domain of said CAR. Preferentially said soluble antigen may be an exogenous antigen. Said exogenous antigen may be applied to the subject that also receive or received the Tregs expressing said CAR for treatment of a disorder as disclosed herein, it is an external stimulant (an external stimulus) that binds to the antigen binding domain of the CAR as disclosed herein and may activate subsequently the Treg cell that expresses said CAR. Said exogenous soluble antigen may be a non-disease causing antigen that evoke no harm to the subject when applied to said subject. The exogenous soluble antigen may be e.g. a macromolecule such as a polypeptide or a polysaccharide that preferentially do not naturally occur in the subject to be treated as disclosed herein.

The soluble antigen, preferentially the exogenous soluble antigen may be selected from the group consisting of macromolecules, such as proteins, polysaccharides, oligo- or polynucleotides, polyethylene-glycols or any other biocompatible polymer compounds which can be applied to humans or derivatives of said molecules, such as small molecular "haptens" bound to the larger marcromolecules. The soluble antigens may be applied in a form that allows activation of the CAR which is typically achieved via cross-linking, i.e. the macromolecules used may contain more than one copy ideally several copies of the actual domain that is bound by the antigen binding domain of the CAR. Such multivalent molecules may induce crosslinking and CAR activation. Preferentially, the only requirement for the (exogenous) soluble antigen is that it can circulate in the circulatory system, e.g. the blood system or lymphatic system and/or the tissue of the subject, that is treated as disclosed herein and is not part of the surface of a cell of said subject with the consequence that the (exogenous) soluble antigen may be bound only by the antigen binding domain of the CAR as disclosed herein that is expressed by the Treg cell when said Treg cell is applied to said subject. Therefore, the (exogenous) soluble antigens may also be immobilized on structures such as beads (nanobeads, microbeads) that allow circulation of the antigen immobilized on such structures in the circulatory system, e.g. the blood system of said subject. These may also be (exogenous) soluble antigens in the meaning of the present invention.

A preferred soluble antigen is dextran (a dextran molecule). Said dextran may be applied to the subject in need to be treated with said Tregs expressing said CAR as a free dextran molecule or immobilized to a particle such as a microbead or nanobead.

Dextran is a complex branched glucan (polysaccharide made of many glucose molecules) composed of chains of varying lengths (from 3 to 2000 kilodaltons). Dextran of any length, e.g. from 3 to 2000 kDa may be used for the herein disclosed applications. Preferentially the dextran used may be over 5, 10, 20, 100 or 200 kDa. In some embodiments of the invention, the dextran used may be a dextran from 60 to 200 kDa. The soluble dextran as used herein may present many antigens for the CAR that binds to dextran as disclosed herein. The dextran may be a poly-antigen instead of a mono-antigen for the anti-dextran CAR.

Said dextran may be unbound dextran, i.e. free dextran, soluble dextran or dextran conjugated to colloidal nano- or microparticles. Said dextran may be administered to a patient in need thereof that harbours the Treg cell as disclosed herein to activate said Treg cell under controllable conditions.

Said dextran may applied also as part of a pharmaceutical composition to a subject (e.g. Deltadex; Dextran 40 10% in NaCl; infusion of e.g 1,5 g dextran per kg bodyweight or less). Alternatively, the dextran may be conjugated to an antibody or another attachment structure, which allows specific targeting of the dextran to cells or tissue matrix surfaces in vivo, e.g. extracellular matrix attachment peptides.

Treg (also named herein as "regulatory T cell" or "Treg cell") are defined here as Foxp3$^+$CD4$^+$ T cells which typically do also express CD25 and lack expression of CD127. Tregs are further characterized by selective expression of CD137 upon activation but lack of CD154 expression as well as lack of effector cytokine expression, e-g- IL-2-IFN-gamma, IL-17, IL-4 etc. within a time window of 4-8 hours of activation. Tregs are also characterized by selective demethylation of specific DNA regions, e.g. within the foxp3 gene region (Treg specific demethylated region, TSDR; see also Huehn, J., et al, 2009, Nat Rev Immunol 9, 83-9) but also other specific methylation patterns in other regions such as the CD25, CTLA4, FANK1, CD137, CD154 gene regions. They represent a separate T cell lineage with highly immunosuppressive functions that are required to maintain tolerance against auto-antigens and harmless foreign antigens. Tcon cells as defined here comprise all CD4+ T cells which are not Treg.

The term "target cell" as used herein refers to cell which may express an antigen on its cell surface that should be recognized (bound) directly or indirectly (e.g. via tagged polypeptide) by the CAR as disclosed herein.

Said target cell may be a cell in a diseased state that causes autoimmunity, transplant rejection, allergy and chronic inflammatory diseases in a subject.

Autoimmunity means a state in which immune cells are directed against self resulting in immune reactions against endogenous structures which can cause autoimmune disease.

Transplant rejection means the generation of immune responses against transplanted tissue which is recognized as foreign by the host's immune system resulting in rejection of the transplanted tissue.

Allergy means the generation of an inappropriate immune response against harmless foreign antigens, being in contact with the subject, e.g. upon inhalation, ingestion or skin contact that can be derived e.g. from the environment or food.

Chronic inflammatory diseases mean the generation of immune reactions against antigens that remain in the system. Examples include immune reactions against bacteria during e.g. inflammatory bowel disease, viruses during chronic infection or endogenous structures during autoimmune reactions. Examples can also include chronic inflammation as a result of allergic reactions against foreign antigens. Autoimmune diseases are a condition arising from autoimmunity resulting in pathologies that can affect multiple different organ systems. Examples include rheumatoid arthritis, multiple sclerosis, neuromyelitis optica, systemic lupus erythematosus, type 1 diabetes or a chronic infection by virus, bacteria, parasite of a subject means the invasion of a subject by disease-causing agents such as virus, bacteria or parasites followed by their replication.

The CARs as disclosed herein (polypeptide(s)), the nucleic acid molecule(s) encoding the CARs, recombinant expression vectors, cells expressing the CARs, and populations of cells expressing the CARs, can be isolated and/or purified. The term "isolated" means altered or removed from the natural state. For example, an isolated population of cells means an enrichment of such cells and separation from other cells which are normally associated in their naturally occurring state with said isolated cells. An isolated population of cells means a population of substantially purified cells which are a more homogenous population of cells than found in nature. Preferably the enriched cell population comprises at least about 90% of the selected cell type. In particular aspects, the cell population comprises at least about 90%, 91%, 92%, 93%, 94%, 95%, 96%, 97%, 98%, 99%, or even 100% of the selected cell type.

For example, a nucleic acid or a peptide naturally present in a living animal is not "isolated", but the same nucleic acid or peptide partially or completely separated from the coexisting materials of its natural state is "isolated". An isolated nucleic acid or protein can also exist in a non-native environment such as, for example, in a host cell.

As used herein, the term "subject" refers to a mammal such as mouse, rat, cow, pig, goat, chicken, dog, monkey or human. Preferentially, the subject is a human. The subject may be a subject suffering from a disorder such as autoimmune disease, allergy, transplant rejection or chronic inflammation (a patient), but the subject may be also a healthy subject.

The term "autologous" as used herein refers to any material derived from the same subject to who it is later re-introduced.

The term "allogeneic" as used herein refers to any material derived from a different subject of the same species as the subject to who the material is re-introduced.

The terms "therapeutically effective amount" or "therapeutically effective population" mean an amount of a cell population which provides a therapeutic benefit in a subject.

The terms "specifically binds" or "specific for" with respect to an antigen binding domain of an antibody, of an antigen binding fragment thereof, as used e.g. in the CAR as disclosed herein, refer to an antigen binding domain which recognizes and binds to a specific antigen, but does not substantially recognize or bind other molecules in a sample. An antigen binding domain that binds specifically to an antigen from one species may bind also to that antigen from another species. This cross-species reactivity is typical to many antibodies and therefore not contrary to the definition of that antigen binding domain as specific. An antigen binding domain that specifically binds to an antigen may bind also to different allelic forms of the antigen (allelic variants, splice variants, isoforms etc.) or homologous variants of this antigen from the same gene family. This cross reactivity is typical to many antibodies and therefore not contrary to the definition of that antigen binding domain as specific.

The terms "engineered cell" and "genetically modified cell" as used herein can be used interchangeably. The terms mean containing and/or expressing a foreign gene or nucleic acid sequence which in turn modifies the genotype and/or phenotype of the cell or its progeny. Especially, the terms refer to the fact that cells, preferentially immune cells can be manipulated by recombinant methods well known in the art to express stably or transiently peptides or proteins which are not expressed in these cells in the natural state. For example, immune cells are engineered to express an artificial construct such as a chimeric antigen receptor on their cell surface.

The term "disorder" means a functional abnormality or disturbance in a subject such as a cancer, an autoimmune disorder, or an infection by virus, bacteria, parasite, or others.

The term "treat" (treatment of) a disorder as used herein means to reduce the frequency or severity of at least one sign or symptom of a disease or disorder experienced by a subject.

Immunotherapy is a medical term defined as the "treatment of disease by inducing, enhancing, or suppressing an immune response". Immunotherapies designed to elicit or amplify an immune response are classified as activation immunotherapies, while immunotherapies that reduce or suppress are classified as suppression immunotherapies. Cancer immunotherapy as an activating immunotherapy attempts to stimulate the immune system to reject and destroy tumors. Adoptive cell transfer uses cell-based cytotoxic responses to attack cancer cells. Immune cells such as T cells that have a natural or genetically engineered reactivity to a patient's cancer are generated in vitro and then transferred back into the cancer patient.

The term "expression" as used herein is defined as the transcription and/or translation of a particular nucleotide sequence driven by its promoter in a cell.

The amino acid sequences of SEQ ID NO:1 and SEQ ID NO:2 as given in the sequence listing protocol are partial sequences of CAR as disclosed herein. Said sequences of SEQ ID NO: 1 and SEQ ID NO:2 may also comprise variants of this sequences, which has some amino acids deleted, added or replaced while still retaining the intended function as described herein. Therefore, included in this definition are variants of the amino acid sequences in SEQ ID NO: 1 and SEQ ID NO:2 such as amino acid sequences essentially similar to SEQ ID NO: 1 and SEQ ID NO:2, having a sequence identity of at least 70%, or at least 75%, 80%, 85%, 90%, 95%, 97%, 98% or 99% at the amino acid sequence level, respectively. In general, all amino acid variations which do not lead to intentional changes of the intended function of the sequence SEQ ID NO: 1 and SEQ ID NO:2 are included under this definition. In the context of the present invention, "sequence identity" may be determined using pairwise alignments using alignments programs for amino acid sequences well known to the art.

The "circulatory system" is an organ system of a subject that permits blood to circulate and transport nutrients (such as amino acids and electrolytes), oxygen, carbon dioxide, hormones, and blood cells to and from the cells in the body to provide nourishment and help in fighting diseases, stabilize temperature and pH, and maintain homeostasis. The circulatory system comprises two separate systems: the cardiovascular system, which distributes blood, and the lymphatic system, which circulates lymph.

The terms "automated method" or "automated process" as used herein refer to any process being automated through the use of devices and/or computers and computer software which otherwise would or could be performed manually by an operator. Methods (processes) that have been automated require less human intervention and less human time to deliver. In some instances a method is automated if at least one step of the method is performed without any human support or intervention. Preferentially the method is automated if all steps of the method are performed without human support or intervention.

The term "particle" as used herein refers to a solid phase such as colloidal particles, microspheres, nanoparticles, or beads. Methods for generation of such particles are well known in the field of the art. The particles may be magnetic particles. The particles may be in a solution or suspension or they may be in a lyophilised state prior to use in the present invention. The lyophilized particle is then reconstituted in convenient buffer before contacting the sample to be processed regarding the present invention.

An especially potent sorting technology is magnetic cell sorting. Methods to separate cells magnetically are commercially available from several suppliers. In a preferred embodiment for enriching, sorting and/or detecting cells in a biological sample comprising cells for e.g. Treg cells and other (immune cells) monoclonal antibodies or antigen binding fragments thereof are used in conjunction with colloidal superparamagnetic microparticles having an organic coating by e.g. polysaccharides (Magnetic-activated cell sorting (MACS®) technology (Miltenyi Biotec, Bergisch Gladbach, Germany)).

Another sorting technology uses flow cytometry. Flow cytometry is a laser- or impedance-based, biophysical technology employed e.g. in cell sorting and biomarker detection by suspending e.g. cells in a stream of fluid and passing them by an electronic detection apparatus. It allows simultaneous multiparametric analysis of the physical and chemical characteristics of up to thousands of particles per second. Fluorescence-activated cell sorting (FACS) is a specialized type of flow cytometry. It provides a method for sorting a heterogeneous mixture of biological cells into two or more containers, one cell at a time, based upon the specific light scattering and fluorescent characteristics of each cell.

As used herein, the terms "depletion", "depleting" and the like, in the context of cell isolation, purification or enrichment, have the normal meaning in the art, and refer to removal of specified cells (e.g., CD154+ cells) from a sample comprising Tregs and other (immune) cells. Method for depletion are well known in the art and are described herein, and include, for example, FACS or MACS sorting in which specified cells in a population (e.g., CD154+ cells) are labeled and removed from the population of cells resulting in a new population in which the specified cells are absent or present in a lower proportion than in the starting population. It will be recognized that "depletion" does not require that the specified cells be entirely removed or that the new population be entirely free of the specified cells. Typically, depleting specified cells from a population means reducing the representation of such cells (measured as a percentage of all of the cells in the population) by at least about 50%, at least about 60%, at least about 70%, at least about 80%, at least about 90%, at least about 95%, at least about 98%, or at least about 99%).

As used herein, the term "positive selection", in the context of cell isolation, purification or enrichment, have the normal meaning in the art, and refer to the enrichment of specified cells (e.g., CD137+ cells) from a sample comprising Tregs and optionally other (immune) cells. Methods for positive selection are well known in the art and are described herein, and include, for example, FACS or MACS sorting in which specified cells in a population (e.g., CD137+ cells) are labeled and isolated from the population of cells in that the isolated cells result in a new population in which the specified cells are present in a higher proportion than in the starting population.

EMBODIMENTS

In one embodiment of the invention a Treg expressing the CAR that comprises the CD3zeta and CD137 signaling domains and an antigen binding domain specific for an exogenous antigen such as dextran is generated. The DNA construct encoding the CAR can be transfected or transduced into a Treg cell by methods well known in the art (e.g. viral-based systems, physical methods, biological methods, chemical methods). Regardless the methods used to integrate, preferentially stably integrate, the nucleic acid encoding the CAR in the Treg cell, as a result the Treg cell expresses the CAR. These Treg cells can be activated in-vitro and in-vivo by addition of dextran to the cells that are in cell culture or circulating in the blood of a subject to whom they have been applied.

In another embodiment of the invention, Tregs expressing the CAR of the invention are isolated after antigen-specific activation with the respective antigen, e.g. dextran by isolation of cells that express CD137 in combination with or without CD154 either by magnetic or fluorescent sorting.

In an embodiment of the invention Tregs can be obtained from a variety of sources such as peripheral blood mononuclear cells (PMBCs), bone marrow, lymph node tissue, cord blood or thymus tissue. For enrichment of these cells methods well known in the art can be used such as centrifugation through a Ficoll™ or PERCOLL™ gradient or positive/negative selection techniques such as fluorescent sorting (e.g. FACSsort) or magnetic sorting (e.g. MACS®).

In one embodiment Tregs of a given source of a subject are magnetically labeled, for example with a magnetic bead coupled to antibodies specific for CD4 and/or CD25 and/or CD127 and/or CD154 and/or CD137, washed, magnetically enriched and collected. Then these Treg cells may be engineered to express the CD137-CD3ζ-CAR on their cell surface.

In another embodiment of the invention an engineered Treg expressing a CAR of the invention is isolated after the transfection/transduction process by methods well known in the art, e.g. fluorescent based separating technologies such as FACS® or magnetic cell separation methods such as MACS®.

In one embodiment of the invention engineered Tregs expressing the CD137-CD3ζ-CAR are expanded in the presence of an exogenous antigen (e.g. dextran) or polyclonal stimulation with anti-CD3/anti-CD28 to increase numbers of engineered Tregs and to increase purity of Tregs expressing CD137-CD3ζ-CAR. Preferentially, said amount of engineered Tregs is increased to a therapeutic effective amount.

In one embodiment of the invention Tregs with high purities (e.g. >80% FoxP3 expression) are genetically engineered to express the CD137-CD3ζ-CAR.

In one embodiment of the invention Tregs with high purities (e.g. >80% FoxP3 expression) are isolated by expression of CD137 in combination with other markers e.g. CD25, CD127, CD154.

In one embodiment of the invention the CD137-CD3ζ-CAR is used for treatment in a subject having an inflammatory disease or autoimmune disease, e.g. inflammatory bowel disease, rheumatoid arthritis, multiple sclerosis, or transplant rejection or graft versus host disease (GvHD).

In one embodiment of the invention the CD137-CD3ζ-CAR is activated by application of an exogenous antigen (e.g. dextran) in soluble or bead-immobilized form either at local sites or systemically, preferentially in patients having an inflammatory disease or autoimmune disease, e.g. IBD, rheumatoid arthritis, MS, transplant rejection, GvHD.

EXAMPLES

Example 1

Generation of Dextran-Specific CAR-Tregs With Different Intracellular Signaling Domains The CAR constructs contain a specific binding fragment that is derived from an antibody specific for an exogenous antigen (e.g. dextran). The hinge region may be derived e.g. from IgG domains, CD8a CD8a, or CD28 and may comprise an epitope/tag allowing for the detection of the CAR. The transmembrane domain may be derived e.g. from CD8a or CD28 followed by one to three signaling domains containing CD3ζ and CD137 as for example shown in FIG. 1A. Tregs are genetically engineered to express the CD137-CD3ζ-CAR which can be determined by expression of LNGFR (FIG. 1B). Antigen-binding of the CD137-CD3ζ-CAR can be determined by incubation with the respective antigen that can be labeled (e.g. fluorescently) as shown for dextran in FIG. 1C.

Example 2

Activation of CAR-Tregs With Different Intracellular Signaling Domains

CAR-Tregs that are specific for an exogenous antigen (e.g. dextran) can be activated by their respective antigen and activation can be analysed by CD137 expression. CAR-Treg activation after stimulation with bead-bound dextran is shown in FIG. 2A. The CD137-CD3ζ-CAR was more potent in inducing CD137 expression in CAR-Tregs (FIG. 2A). Functionality of other tested CAR-constructs with the same specificity was analysed by phosphorylation of ZAP70. Phosphorylated ZAP70 was detected in CAR-Tregs with e.g. CD28-CD3ζ signaling (FIG. 2B), but only the CD137-CD3ζ-CAR induced Treg activation (FIG. 2A).

Example 3

Expansion of Dextran-Specific CAR-Tregs With Different Intracellular Signaling Domains CAR-Tregs that are specific for an exogenous antigen (e.g. dextran) can be expanded in the presence of anti-CD3/-CD28 (FIG. 3A, C) or their respective antigen, e.g. bead-bound dextran (FIG. 3B, D). Only CAR-Tregs with the CD137-CD3ζ-CAR expanded showing superior functionality of the CD137-CD3ζ-CAR.

Example 4

Comparison of Different Intracellular Signaling Domains in Tregs and Tcons

CAR-Tregs and CAR-Tcons were generated expressing the anti-dextran CAR with different co-stimulatory domains in combination with CD3z. Dextran-binding was similar between constructs (FIG. 4A), but different signaling domains had a different impact of Treg and Tcon activation. Treg activation was analysed by CD137 expression and Tcon activation by CD154 expression. CAR-Tregs were activated most efficiently with CD137-CD3z and CAR-Tcon with CD28-CD3z (FIG. 4B).

Example 5

Isolation of Antigen-Specific CAR-Tregs

CAR-Tregs with the CD137-CD3z CAR were isolated by LNGFR expression or by
CD137 expression after 6 h stimulation with dextran. Transgene (FIG. 5A) and receptor expression (FIG. 5B) were similar between both sorting strategies, but antigen-specific restimulation was highly efficient when CAR-Tregs were sorted by CD137 expression (FIG. 5C).

Methods

CAR Constructs

All CAR-constructs contained an AC146-derived scFv, a CD8 transmembrane domain, a XS IgG4 hinge and a P2A-linked ΔLNGFR for detection of transfected and transduced cells. Lentiviral supernatants were generated by co-transfection of HEK293T cells with the expression vector and packaging plasmids. One day prior to transfection, $3 \times 10^6$ HEK293T cells were seeded in a 10cm cell culture dish in complete DMEM (cDMEM) consisting of DMEM (Gibco®), +10% FCS+100 U/ml penicillin, 100 μg/ml streptomycin+50 μM 2-Mercaptoethanol (all Thermo Fisher Scientific, Schwerte, Germany). Cells were transiently transfected with 0.84 μg pMDG-2.VSV-G, 5.16 μg pCMVΔR8.74 and 3.35 μg Dextran-CAR plasmids diluted in ddH2O supplemented with 2.5M CaCl2. While aerating, 2 ml of 2×HBS buffer (136.89 mM NaCl, 4.96 mM KCl, 1.76 mM Na2HPO4, 20.98 mM HEPES in ddH2O, pH=6.75-6.76) were slowly added to the solution and 2 ml of the transfection solution was added dropwise to the cells. The medium containing the transfection solution was removed after 4 h and cells were washed twice with pre-warmed PBS before fresh cDMEM was added. After 48 hours, lentiviral supernatants were harvested, filtered (0.45 μm) and used directly or stored at −80° C. for up to 6 months.

Treg Isolation and Transduction

Leukapheresis products from healthy donors were obtained from the Charité University hospital, Berlin, Germany with informed consent according to ethical guidelines. PBMC were obtained by Ficoll-Paque (GE Healthcare Life Sciences, Freiburg, Germany) gradient centrifugation. CD25+ Treg were isolated from PBMC according to manufacturer's recommendations using CD25 microbeads (Miltenyi Biotec, Bergisch Gladbach, Germany). Treg were cultured in "Treg expansion medium" consisting of TexMACS medium (Miltenyi Biotec, Bergisch Gladbach, Germany) +5% (v/v) human AB-serum (Sigma-Aldrich, Schnelldorf, Germany) +100 U/ml IL-2+100 nmol rapamycin (both Miltenyi Biotec, Bergisch Gladbach, Germany) and 100 U/ml penicillin/100 μg/ml streptomycin (Gibco®, Thermo Fisher Scientific, Schwerte, Germany) in the presence of Treg expansion beads (Miltenyi Biotec, Bergisch Gladbach, Germany) at a bead-to-cell ratio of 4:1. CD4+ Tcons were activated in TexMACS medium (Miltenyi Biotec, Bergisch Gladbach, Germany) +5% (v/v) human AB-serum (Sigma-Aldrich, Schnelldorf, Germany) +200 U/ml IL-2 in the presence of 30 ng/ml anti-CD3 and 1 μg/ml anti-CD28. On d3, culture medium was replaced with the respective lentiviral supernatants supplemented with 4 μg/ml protaminsulfate and cells were spinoculated on retronectin-coated 96 well plates for 90 min at 800 g and 32° C. After centrifugation, viral supernatant was removed and fresh culture medium was added to the cells. Transduction efficiency was assessed on d2 or d3 after transduction by staining of LNGFR on the cellular surface. Tregs and Tcons were expanded for 10-12 days and medium was replaced every 2-3 days. Cells were rested for 2 days without stimulation in RPMI-1640 (Gibco®, Thermo Fisher Scientific, Schwerte, Germany) +5% (v/v) human AB-serum (Sigma-Aldrich, Schnelldorf, Germany) +100 U/ml penicillin/100 µg/ml streptomycin (Gibco®, Thermo Fisher Scientific, Schwerte, Germany) before 6 h restimulation with Treg expansion beads (4:1 bead-to-cell ratio, Miltenyi Biotec, Bergisch Gladbach, Germany), soluble FITC Dextran (MW: 2,000,000, 2 µg/ml, Sigma-Aldrich, Schnelldorf, Germany), bead-bound dextran (1:100; dextran-coated microbeads in PBS, Miltenyi Biotec, Bergisch Gladbach, Germany) or 10 ng/ml PMA and 500 ng/ml Ionomycin (Sigma-Aldrich, Schnelldorf, Germany).

Flow Cytometry

Cells were stained in different combinations with the following antibodies according to manufacturer's recommendations: CD4-PE-Vio770, CD4-APC-Vio-770, CD4-FITC, CD4-VioBlue (VIT4), CD25-VioBright FITC (4E3), CD127-FITC, CD127-PE-Vio770 (MB15-18C9), CD271 (LNGFR)-PE, CD271 (LNGFR)-PE-Vio770 (ME20.4-1.H4), CD137-PE (4B4-1), CD154-APC, CD154-VioBlue (5C8) (all Miltenyi Biotech, Bergisch Gladbach, Germany), Viobility 405/520 Fixable Dye (Miltenyi Biotech, Bergisch Gladbach, Germany) or propidium iodide (Sigma-Aldrich, Schnelldorf, Germany) were used to exclude dead cells. For staining of CAR surface expression, Treg were incubated for 10 min with 2 µg/ml FITC-labeled dextran (MW: 2,000,000, Sigma-Aldrich, Schnelldorf, Germany) at 4° C. together with labeling of other surface molecules. All data were acquired on a FACS Canto/LSRII (BD, Heidelberg, Germany) or MACS Quant Analyzer (Miltenyi Biotec, Bergisch Gladbach, Germany) and FACS sorting was performed on an Aria I, Aria II or Influx Cell Sorter (BD, Heidelberg, Germany). FlowJo (TreeStar, Inc, Ashland, OR, USA) was used for data analysis.

Quantification of Gene Expression

The competitive expansion of Dex-CAR constructs with different signaling domains was analysed by quantitative real-time PCR. DNA was isolated by Zymo Research Quick-DNA™ Miniprep Kit (Zymo Research, Freiburg, Germany) according to manufacturer's instructions and gene expression was analysed using 1× SYBR® Green PCR Master Mix (Thermo Fisher Scientific, Schwerte, Germany) and 500 nMol forward and reverse primers (TIB MOLBIOL, Berlin), respectively. Gene expression was analysed on a StepOne™ Real-Time PCR System (Thermo Fisher Scientific, Schwerte) and normalized to expression of GAPDH.

REFERENCES

Blat D, Zigmond E, Alteber Z, Waks T, Eshhar Z (2014) Suppression of murine colitis and its associated cancer by carcinoembryonic antigen-specific regulatory T cells. Mol Ther 22 (5):1018-1028. doi:10.1038/mt.2014.41

Boardman D A, Philippeos C, Fruhwirth G O, Ibrahim M A, Hannen R F, Cooper D, Marelli-Berg F M, Watt F M, Lechler R I, Maher J, Smyth L A, Lombardi G (2017) Expression of a Chimeric Antigen Receptor Specific for Donor HLA Class I Enhances the Potency of Human Regulatory T Cells in Preventing Human Skin Transplant Rejection. Am J Transplant 17 (4):931-943. doi:10.1111/ajt.14185

Elinav E, Adam N, Waks T, Eshhar Z (2009) Amelioration of colitis by genetically engineered murine regulatory T cells redirected by antigen-specific chimeric receptor. Gastroenterology 136 (5):1721-1731. doi:10.1053/j.gastro.2009.01.049

Elinav E, Waks T, Eshhar Z (2008) Redirection of regulatory T cells with predetermined specificity for the treatment of experimental colitis in mice. Gastroenterology 134 (7):2014-2024. doi:10.1053/j.gastro.2008.02.060

Golshayan D, Jiang S, Tsang J, Garin M I, Mottet C, Lechler R I (2007) In vitro-expanded donor alloantigen-specific CD4+CD25+ regulatory T cells promote experimental transplantation tolerance. Blood 109 (2):827-835. doi:10.1182/blood-2006-05-025460

Gross G, Waks T, Eshhar Z (1989) Expression of immunoglobulin-T-cell receptor chimeric molecules as functional receptors with antibody-type specificity. Proc Natl Acad Sci USA 86 (24):10024-10028

Joffre O, Santolaria T, Calise D, Al Saati T, Hudrisier D, Romagnoli P, van Meerwijk J P (2008) Prevention of acute and chronic allograft rejection with CD4+CD25+Foxp3+ regulatory T lymphocytes. Nat Med 14 (1):88-92. doi:10.1038/nm1688

Kuwana Y, Asakura Y, Utsunomiya N, Nakanishi M, Arata Y, Itoh S, Nagase F, Kurosawa Y (1987) Expression of chimeric receptor composed of immunoglobulin-derived V regions and T-cell receptor-derived C regions. Biochem Biophys Res Commun 149 (3):960-968

MacDonald K G, Hoeppli R E, Huang Q, Gillies J, Luciani D S, Orban P C, Broady R, Levings M K (2016) Alloantigen-specific regulatory T cells generated with a chimeric antigen receptor. J Clin Invest 126 (4):1413-1424. doi:10.1172/JCI82771

Masteller E L, Warner M R, Tang Q, Tarbell K V, McDevitt H, Bluestone J A (2005) Expansion of functional endogenous antigen-specific CD4+CD25+ regulatory T cells from nonobese diabetic mice. J Immunol 175 (5):3053-3059

Mekala D J, Geiger T L (2005) Immunotherapy of autoimmune encephalomyelitis with redirected CD4+CD25+ T lymphocytes. Blood 105 (5):2090-2092. doi:10.1182/blood-2004-09-3579

Nishimura E, Sakihama T, Setoguchi R, Tanaka K, Sakaguchi S (2004) Induction of antigen-specific immunologic tolerance by in vivo and in vitro antigen-specific expansion of naturally arising Foxp3+CD25+CD4+ regulatory T cells. Int Immunol 16 (8):1189-1201. doi:10.1093/intimm/dxh122

Noyan F, Zimmermann K, Hardtke-Wolenski M, Knoefel A, Schulde E, Geffers R, Hust M, Huehn J, Galla M, Morgan M, Jokuszies A, Manns MP, Jaeckel E (2017) Prevention of Allograft Rejection by Use of Regulatory T Cells With an MHC-Specific Chimeric Antigen Receptor. Am J Transplant 17 (4):917-930. doi:10.1111/ajt.14175

Putnam A L, Safinia N, Medvec A, Laszkowska M, Wray M, Mintz M A, Trotta E, Szot G L, Liu W, Lares A, Lee K, Laing A, Lechler R I, Riley J L, Bluestone J A, Lombardi G, Tang Q (2013) Clinical grade manufacturing of human alloantigen-reactive regulatory T cells for use in transplantation. Am J Transplant 13 (11):3010-3020. doi:10.1111/ajt.12433

Sagoo P, Ali N, Garg G, Nestle F O, Lechler R I, Lombardi G (2011) Human regulatory T cells with alloantigen specificity are more potent inhibitors of alloimmune skin graft damage than polyclonal regulatory T cells. Sci Transl Med 3 (83):83ra42. doi:10.1126/scitranslmed.3002076

Skuljec J, Chmielewski M, Happle C, Habener A, Busse M, Abken H, Hansen G (2017) Chimeric Antigen Receptor-Redirected Regulatory T Cells Suppress Experimental Allergic Airway Inflammation, a Model of Asthma. Front Immunol 8:1125. doi:10.3389/fimmu.2017.01125

Taylor P A, Lees C J, Blazar B R (2002) The infusion of ex vivo activated and expanded CD4(+)CD25(+) immune regulatory cells inhibits graft-versus-host disease lethality. Blood 99 (10):3493-3499

Trenado A, Charlotte F, Fisson S, Yagello M, Klatzmann D, Salomon B L, Cohen J L (2003) Recipient-type specific CD4+CD25+ regulatory T cells favor immune reconstitution and control graft-versus-host disease while maintaining graft-versus-leukemia. J Clin Invest 112 (11):1688-1696. doi:10.1172/JC117702

Yoon J, Schmidt A, Zhang A H, Konigs C, Kim Y C, Scott D W (2017) FVIII-specific human chimeric antigen receptor T-regulatory cells suppress T- and B-cell responses to FVIII. Blood 129 (2):238-245. doi:10.1182/blood-2016-07-727834

---

The invention claimed is:

1. A combination of pharmaceutical compositions comprising
   i) a population of human Treg cells expressing a CAR together with a pharmaceutical acceptable carrier, the CAR comprising
      a) at least one antigen binding domain,
      b) a transmembrane domain,
      c) a cytoplasmic signaling domain comprising at least one primary cytoplasmic signaling domain and at least the co-stimulatory signaling domain of CD137, wherein said at least one antigen binding domain specifically binds dextran; and
   ii) a dextran molecule that is not conjugated to an antibody or another attachment structure which allows specific targeting of the dextran to cells or tissue matrix surfaces in vivo,
   thereby allowing the activation of said Treg cell upon binding of dextran to said at least one antigen binding domain of said CAR.

2. The composition according to claim 1 for treatment of an autoimmune disease, allergy, transplant rejection, graft versus host disease, chronic inflammatory diseases, inflammatory bowel diseases, or a chronic infection by virus, bacteria, or parasite.

* * * * *

SEQUENCE LISTING

```
<160> NUMBER OF SEQ ID NOS: 2

<210> SEQ ID NO 1
<211> LENGTH: 117
<212> TYPE: PRT
<213> ORGANISM: Artificial sequence
<220> FEATURE:
<223> OTHER INFORMATION: anti-dextran VH

<400> SEQUENCE: 1

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Pro Tyr Tyr Tyr Thr Ser Ser Ile Val Trp Gly Thr Gly Thr Thr
            100                 105                 110

Val Thr Val Ser Ala
        115

<210> SEQ ID NO 2
<211> LENGTH: 106
<212> TYPE: PRT
<213> ORGANISM: Artificial sequence
<220> FEATURE:
<223> OTHER INFORMATION: anti-dextran VL

<400> SEQUENCE: 2

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80
```

```
Asp Ala Ala Thr Tyr Tyr Cys Gln Gln Trp Ser Ser Asn Pro Leu Thr
                85              90                  95

Phe Gly Ala Gly Thr Lys Leu Glu Leu Lys
            100             105
```